United States Patent [19]
Henderson et al.

[11] Patent Number: 6,001,555
[45] Date of Patent: Dec. 14, 1999

[54] METHOD FOR IDENTIFYING AND USING COMPOUNDS THAT INACTIVATE HIV-1 AND OTHER RETROVIRUSES BY ATTACKING HIGHLY CONSERVED ZINC FINGERS IN THE VIRAL NUCLEOCAPSID PROTEIN

[75] Inventors: Louis E. Henderson, Mt. Airy; Larry O. Arthur, Walkersville; William G. Rice, Frederick; Alan R. Rein, Takoma Park, all of Md.

[73] Assignee: The United States of America as represented by the Department of Health and Human Services, Washington, D.C.

[21] Appl. No.: 08/379,420

[22] Filed: Jan. 27, 1995

Related U.S. Application Data

[63] Continuation-in-part of application No. 08/312,331, Sep. 23, 1994, abandoned.

[51] Int. Cl.[6] .................................................... C12Q 1/70
[52] U.S. Cl. .................. 435/5; 424/207.1; 424/208.1; 422/61
[58] Field of Search ...................... 435/5, 69.1; 436/808; 568/21, 25, 419; 548/548

[56] References Cited

U.S. PATENT DOCUMENTS

| | | | |
|---|---|---|---|
| 5,262,564 | 11/1993 | Kun et al. | 562/430 |
| 5,464,871 | 11/1995 | Kun et al. | 514/617 |
| 5,482,975 | 1/1996 | Kun et al. | 514/619 |
| 5,484,951 | 1/1996 | Kun et al. | 549/285 |
| 5,516,941 | 5/1996 | Kun et al. | 564/166 |
| 5,519,053 | 5/1996 | Kun et al. | 514/457 |

OTHER PUBLICATIONS

Rice, W.G. et al., *Science* 270:1194–1196 (1995).
Wondrak, E.M. et al., *Journal of Biological Chemistry*, 269:21948–21950 (1995).
Yu, X. et al., *Chemical Research in Toxicology*, 8:586–590 (1995).
Coffin, J., 1996, "Retroviridae: The Viruses and Their Replication", in *Fields Virology*, Third Edition, Fields et al., eds., Lippincott–Raven Publishers, Philadelphia, pp. 1769 and 1770.
Rice et al., 1995, "Discovery and in Vitro Development of AIDS Antiviral Drugs as Biopharmaceuticals", Adv. Pharmacol. 33:389–438.
Wyand, M., 1992, "The Use of SIV–Infected Rhesus Monkeys for the Preclinical Evaluation of AIDS Drugs and Vaccines", AIDS Res. Human Retro. 8:349–356.
Flexner et al., 1997, "Pharmacology of Antiretroviral Agents", in *AIDS: Biology, Diagnosis, Treatment, and Prevention,* fourth edition, DeVita et al., eds., Lippincott–Raven Publishers, pp. 479–493.
Mellors, J., 1996, "Closing in on human immunodeficiency virus–1", Nature Med. 2:274–275.
J.M. Berg, *Science* 232, 485 (1986).
J.W. Bess, Jr., et al., *J. Virol.* 66, 840 (1992).
M.R. Chance et al., *Proc. Natl. Acad. Sci. U.S.A.* 89, 10041 (1992).
T.L. South, and M.F. Summers, *Adv. Inorg. Biochem.* 8, 199 (1990).
T.L. South, et al., *Biochem. Pharmacol.* 40, 123 (1990) (see Figure 1).
A. Aldovini and R.A. Young, *J. Virol.* 64, 1920 (1990).
R.J. Gorelick et al., *J. Virol.* 64, 3207 (1990).
W.G. Rice et al., *Nature* 361, 473 (1993).
W.G. Rice et al. *PNAS* 90, 9721 (1993).
K.G. Buki, et al., *FEBS Letters* 290, 181 (1991).
Jentoft et al., 1988, "Conserved cysteine and histidine residues of the avian myeloblastosis virus nucleocapsid protein are essential for viral replication but are not "zinc–binding fingers"", Proc. Natl. Acad. Sci. USA 85:7094–7098.
Rice et al., 1993, "Inhibition of HIV–1 infectivity by zinc–ejecting aromatic C–nitroso compounds", Nature (London) 361:473–475.
Nagelkerke et al., 1991, "Role of microtubuli in secretion of very–low–density lipoprotein in isolated rat hepatocytes: e3/02/96cts of thiol reagents", Hepatology 14:1259–1268.
Johnston and Hoth, 1993, "Present status and future prospects for HIV therapies", Science 260:1286–1293.

*Primary Examiner*—Frank C. Eisenschenk
*Assistant Examiner*—Jeffrey S. Parkin
*Attorney, Agent, or Firm*—Townsend and Townsend and Crew LLP

[57] ABSTRACT

The present invention provides several classes of compounds which can be used to inactivate retroviruses, such as HIV-1, by attacking the CCHC zinc fingers of the viral nucleocapsid protein and ejecting the zinc therefrom. In addition, kits for identifying compounds that can react with CCHC zinc fingers of the nucleocapsid proteins of a large number of different retroviruses have also been developed. The kits of the present invention describe a set of specific tests and reagents that can be used to screen and identify compounds based on their ability to react with and disrupt retroviral zinc fingers in the viral NC proteins and, in turn, inactivate the retrovirus of interest.

28 Claims, 15 Drawing Sheets

Conservation of CCHC Type Retroviral Zinc Fingers
(-Cys-(X)₂-Cys-(X)₄-His-(X)₄-Cys-)
Amoung Known Retroviruses

HIV-1$_{MN}$ Nucleocapsid Protein first array     linker     second array

MQRGNFRNQRKIIKCFNCGKEGHIAKNCRAPRKRGCWKCGKEGHQMKDCTERQAN

Total Residues..........55
Basic Residues.........15
Acid Residues.......... 4
Net Charge............ +11
IEP.....................10.77

Molecular
Weight.................6451.5
280nm Molar
Absorption. ..........6050

First Zinc Finger

Second Zinc Finger

Figure 4

The Initial Reaction With NEM Modifies
The First Cys Residue In The Second Finger

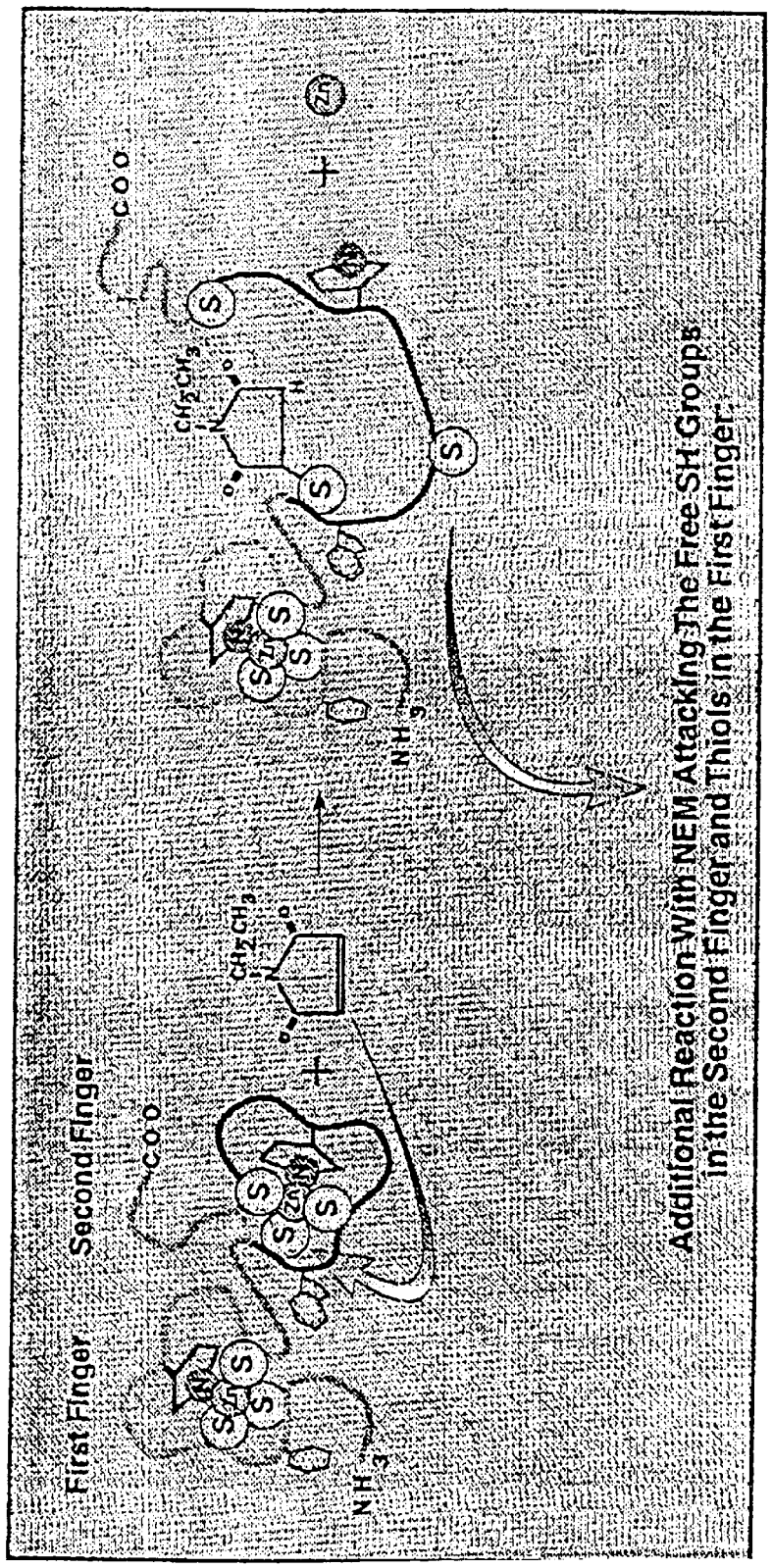

By reacting p7NC with limiting amounts of NEM and analyzing as in Fig. 6, it was determined that the first cysteine in the second zinc finger reacts fastest with the reagent. This is an example showing how the procedures have been used to investigate the reaction pathway and to determine the most reactive thiol in the NC protein.

FIGURE 6

REACTIONS OF HIV-1 NC RETROVIRAL CCHC ZINC FINGERS

Reagent        Reaction With p7NC

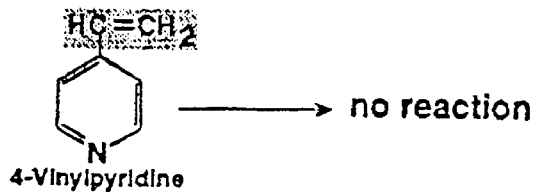 → no reaction

4-Vinylpyridine

 → S-Alkylation

Iodoacetamide

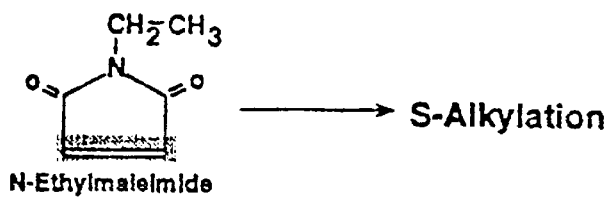 → S-Alkylation

N-Ethylmaleimide $Cu^{+2}$ → oxidation to disulfides $Fe^{+3}$ → oxidation to disulfides

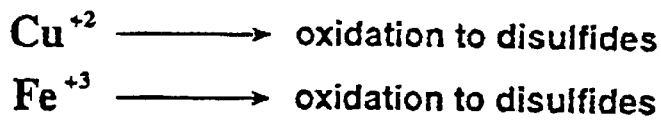 → oxidation to disulfides

3-Nitroso Benzamide (NOBA)

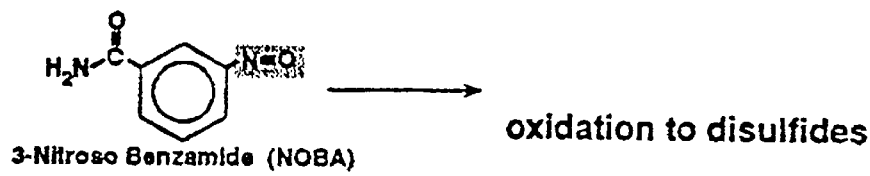 → oxidation to disulfides 5,5'-Dithio-bis-(2-Nitrobenzoic Acid) (DTNB)

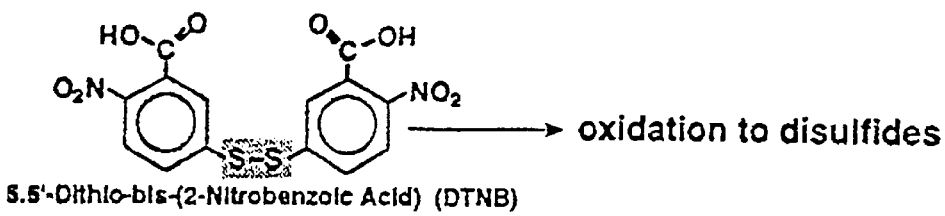 → no reaction

The reactive funtional groups are shaded 

Figure 7
Functional Groups Which React With Retroviral Zinc Fingers
disulfides    R—S—S—R
nitroso compounds    R—N=O
maleimides    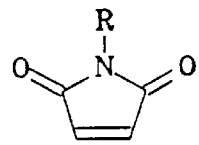
α-halogenated ketones    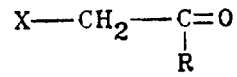
phenylhydrazids    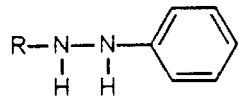
Nitric Oxide and Derivitives    NO
cupric ions and complexes    $Cu^{+2}$
ferric ions and complexes    $Fe^{+3}$
wherein R is any atom or molecule, and X is selected from the group consisting of F, I, Br and Cl.

HPLC Chromatograms of NOBA and Cupric Oxidation Products of p7NC

HPLC Analysis Of p7NC Reactions With Imuthiol and Disulfiram

FIGURE 14
Medical Use and Chemistry of Thiurams
Synthesis
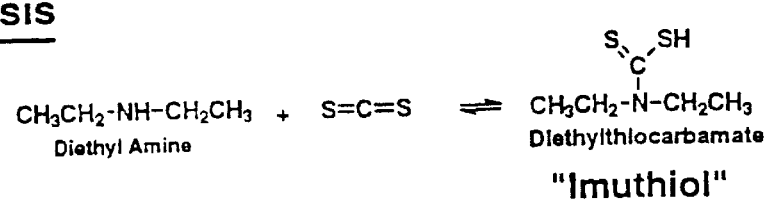
Diethyl Amine → Diethylthiocarbamate
"Imuthiol"
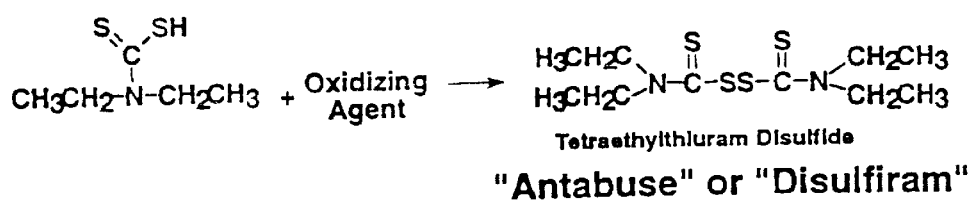
Tetraethylthiuram Disulfide
"Antabuse" or "Disulfiram"
General Reactions
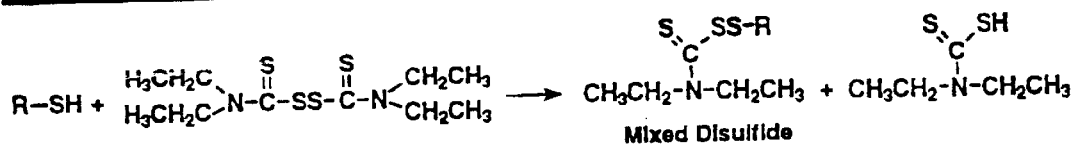
Mixed Disulfide
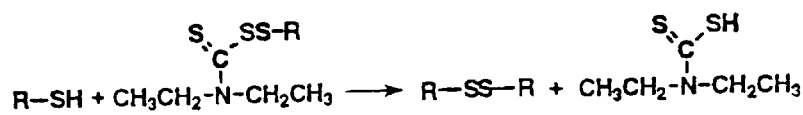
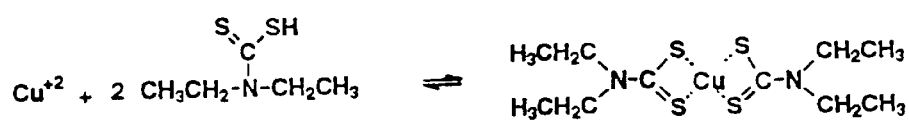

METHOD FOR IDENTIFYING AND USING COMPOUNDS THAT INACTIVATE HIV-1 AND OTHER RETROVIRUSES BY ATTACKING HIGHLY CONSERVED ZINC FINGERS IN THE VIRAL NUCLEOCAPSID PROTEIN

RELATED APPLICATION INFORMATION

This application is a continuation-in-part application of U.S. Ser. No. 08/312,331, filed Sep. 23, 1994, now abandoned, which is incorporated herein by reference in its entirety for all purposes.

BACKGROUND OF THE INVENTION

Most antiviral drugs used to control the spread of HIV-1 have proven to be of limited use because under the selection pressure of the drug, the virus soon mutates to a drug-resistant strain. This tendency to develop drug resistance is a survival strategy used by many classes of viruses and is particularly pronounced among the members of the retrovirus family. One way to defeat this survival strategy is to focus on drugs attacking specific elements of the virus that are intolerant to mutations. Such elements can be identified by searching the proteins present in all viruses within the virus class to identify common or highly conserved structures.

A search of all known retroviruses reveals a highly conserved structure in their nucleocapsid (NC) proteins. All NC proteins of the Oncovirinae and Lentivirinae subfamilies of Retroviridae contain sequences of 14 amino acids with 4 invariant residues, $Cys(X)_2Cys(X)_4His(X)_4Cys$ (L. E. Henderson et al. *J. Biol. Chem.* 256, 8400 (1981)), which chelate zinc through histidine imidazole and cysteine thiolates with a $K_d$ less than $10^{-13}$ (J. M. Berg, *Science* 232, 485 (1986); J. W. Bess, Jr., et al.,*J. Virol.* 66, 840 (1992); M. R. Chance et al., *Proc. Natl. Acad. Sci. U.S.A.* 89, 10041 (1992); T. L. South and M. F. Summers, *Adv. Inorg. Biochem.* 8, 199 (1990); T. L. South, et al., *Biochem. Pharmacol.* 40, 123 (1990)) (see, FIG. 1). These structures are referred to as retroviral CCHC zinc fingers, and are one of the most highly conserved features of retroviruses. Examples of retroviruses which possess at least one CCHC type zinc finger per nucleocapsid protein include, but are not limited to, HIV-1, HIV-2, SIV, BIV, EIAV, Visna, CaEV, HTLV-1, BLV, MPMV, MMTV, RSV, MuLV, FeLV, BaEV, and SSV. The distribution of CCHC zinc fingers among known subgroups of retroviruses is indicated by the diagram set forth in FIG. 1. Due to their highly conserved nature, it is thought that CCHC zinc fingers perform an essential function in viral infectivity. In fact, it has been discovered that mutations of the chelating residues (CCHC) in the zinc fingers yield a non-infectious virus.

HIV-1 NC contains two zinc fingers separated by only 7 amino acids (L. E. Henderson et al., *J. Virol.* 66, 1856 (1992)). The location of the CCHC zinc fingers in the HIV-1 NC protein is indicated in the diagram shown in FIG. 2 (see also, Henderson et al., *J. Virology*, supra, 1992). The zinc fingers are not only required for packaging genomic RNA, but are also essential for early events in virus infection. Both fingers are essential for infectivity (A. Aldovini and R. A. Young, *J. Virol.* 64, 1920 (1990); R. J. Gorelick et al., *J. Virol.* 64, 3207 (1990).

Incubation of HIV-1 with 3-nitrosobenzamide (NOBA), a C-nitroso compound, results in the loss of zinc from the HIV-1 CCHC zinc finger array and viral inactivation (W. G. Rice et al., *Nature* 361, 473 (1993); W. G. Rice et al. *PNAS* 90, 9721 (1993)). Moreover, removal of zinc from the eukaryotic CCHC zinc finger of poly(ADP-ribose) polymerase by C-nitroso compounds has been reported (K. G. Buki, et al., *FEBS Letters* 290, 181 (1991)). Unfortunately, to date, the mechanism by which such CCHC zinc fingers are disrupted has not been discovered. Without an understanding of the reaction mechanism, investigators have had no way to predict which compounds would be effective in selectively disrupting CCHC zinc fingers.

In view of the foregoing, there exists a need in the art for a mechanism and method which can be used to predict compounds that can effectively disrupt CCHC zinc fingers and, in turn, inactivate the retrovirus of choice.

SUMMARY OF THE INVENTION

The mechanism by which the CCHC zinc fingers of retroviral nucleocapsid proteins are disrupted has now been discovered. This mechanism provides investigators with a means of predicting which compounds can effectively disrupt the CCHC zinc fingers and, in turn, inactivate the retrovirus of interest. In addition, it is now discovered that these compounds work in combination with other anti retroviral agents. For instance, the compounds which inactivate the retroviral NC zinc finger appear to show synergistic inactivation (i.e., inactivation which is greater than the sum of the inhibitory activity provided by AZT and a NC zinc finger inactivator separately) of the retrovirus when used in combination with AZT in tissue culture.

The mechanism by which CCHC zinc fingers are disrupted by a nitroso reagent is set forth in FIG. 3. In the first stage, thiolates in each of the two zinc fingers of the NC protein of HIV-1 (p7NC), for example, donate electrons to form a disulfide with the elimination of zinc (see, part A in FIG. 3). This requires two electrons and can proceed via adducts in successive single-electron steps, or, alternatively, via a two-electron transfer to hydroxylaminobenzamide (HABA) directly. The data obtained thus far do not distinguish these possibilities; however, initial adducts (if formed) are short lived, because the rate of HABA production closely follows the rate of loss of p7NC zinc fingers. Remaining thiols are free to react with additional reagent to form adducts that can proceed to react with free thiols to form other disulfides. The disulfide pattern depicted in FIG. 3 is arbitrary, but specific disulfides are formed.

The zinc finger can also react with alkylating agents such as N-ethylmaleimide (NEM). In this process, the initial reaction product is stable and can be isolated and analyzed. As shown in FIG. 4, the initial attack on the zinc finger by NEM occurs on the first thiol of the second zinc finger.

Based upon the foregoing, several classes of compounds have now been discovered which can be used to inactivate HIV-1 by attacking the CCHC zinc fingers and ejecting the zinc therefrom. Moreover, kits for identifying compounds that can react with HIV-1 CCHC zinc fingers are also described. In particular, the kits of the present invention describe a set of specific tests and reagents that can be used to screen and identify compounds based on their ability to react with and disrupt retroviral zinc fingers in the viral NC proteins. Compounds identified using the kits of the present invention are either lead compounds for the development of anti-retroviral drugs or, alternatively, candidates for anti-retroviral drugs.

The kits of the present invention are also used to search through existing repositories of compounds, or individual compounds from any source, to identify those which can be used in the development of new classes of anti-retroviral drugs targeted against viral NC proteins. Not every compound showing reactivity with the fingers will be able to "reach" and attack the fingers in the virus, and, in addition, some are toxic. However, identifying reagents that can react with retroviral CCHC zinc fingers enables rational drug design aimed at attacking this essential element of a retrovirus such as HIV-1. The kits of the present invention can be used to analyze the effects of various compounds on the CCHC zinc fingers of any retrovirus.

More particularly, in one embodiment of the present invention, a method is provided for dissociating a zinc ion from a CCHC zinc finger of a retroviral nucleocapsid protein, the method comprising contacting the retroviral nucleocapsid protein with a compound selected from the group consisting of:

disulfides having the formula R—S—S—R;
maleimides having the formula

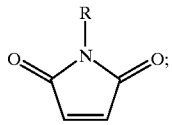

α-halogenated ketones having the formula

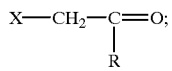

hydrazides having the formula R—NH—NH—R nitric oxide and derivatives containing the NO group;

cupric ions and complexes containing $Cu^{+2}$; and ferric ions and complexes containing $Fe^{+3}$;

wherein R is any atom or molecule, and X is a halogen, e.g., F, I, Br and Cl. The retroviral nucleocapsid protein is incorporated into an intact retrovirus or, alternatively, it is dissociated from the intact retrovirus. An example of such a retroviral nucleocapsid protein is the HIV-1 nucleocapsid protein.

In addition, the present invention provides methods for detecting the dissociation of a zinc ion from the CCHC zinc finger of a retroviral nucleocapsid protein. Such methods include, but are not limited to, the following: capillary electrophoresis, immuno-blotting, Nuclear Magnetic Resonance (NMR), high pressure liquid chromatography (HPLC), detecting release of radioactive zinc-65, detecting fluorescence, and detecting a gel mobility shift.

In another embodiment, the present invention provides a method for inactivating a retrovirus, the method comprising contacting a retrovirus with a compound selected from the group consisting of:

disulfides having the formula R—S—S—R;
maleimides having the formula

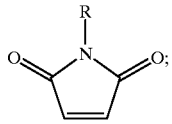

α-halogenated ketones having the formula

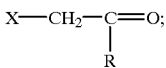

hydrazides having the formula R—NH—NH—R nitric oxide and derivatives containing the NO group;

cupric ions and complexes containing $Cu^{+2}$; and ferric ions and complexes containing $Fe^{+3}$;

wherein R is any atom or molecule, and X is a halogen, e.g., F, I, Br and Cl. Examples of such disulfide compounds include, but are not limited to, the following: Tetramethylthiuram Disulfide, Tetraethylthiuram Disulfide, Tetraisopropylthiuram Disulfide, Tetrabutylthiuram Disulfide, Dicyclopentamethylenethiuram Disulfide, Isopropylxanthic Disulfide, O,O-Diethyl Dithiobis-(Thioformate), Benzoyl Disulfide, Benzoylmethyl Disulfide, Formamidine Disulfide 2HCl, 2-(Diethylamino)ethyl Disulfide, Aldrithiol-2, Aldrithiol-4, 2,2-Dithiobis(Pyridine N-Oxide), 6,6-Dithiodinicotinic Acid, 4-Methyl-2-Quinolyl Disulfide, 2-Quinolyl Disulfide, 2,2-Dithiobis(benzothiazole), 2,2-Dithiobis(4-Tert-Butyl-1-Isopropyl)-Imidazole, 4-(dimethylamino)phenyl disulfide, 2-Acetamidophenyl Disulfide, 2,3-Dimethoxyphenyl Disulfide, 4-Acetamidophenyl Disulfide, 2-(Ethoxycarboxamido) phenyl Disulfide, 3-Nitrophenyl Disulfide, 4-Nitrophenyl Disulfide, 2-Aminophenyl Disulfide, 2,2-Dithiobis (benzonitrile), p-Tolyl Disulfoxide, 2,4,5-Trichlorophenyl Disulfide, 4-Methylsulfonyl-2-Nitrophenyl Disulfide, 4-Methylsulfonyl-2-Nitrophenyl Disulfide, 3,3-Dithiodipropionic Acid, N,N-Diformyl-L-Cystine, Trans-1, 2-Dithiane-4,5-Diol, 2-Chloro5-Nitrophenyl Disulfide, 2-Amino-4-Chlorophenyl Disulfide, 5,5-Dithiobis(2-Nitrobenzoic Acid), 2,2-Dithiobis(1-Naphtylamine), 2,4-Dinitrophenyl p-Tolyl Disulfide, 4-Nitrophenyl p-Tolyl Disulfide, and 4-Chloro-3-Nitrophenyl Disulfideformamidine disulfide dihydrochloride. An example of a maleimide is N-Ethylmaleimide. An example of a hydrazide is 2-(Carbamoylthio)-Acetic Acid 2-Phenylhydrazide. Retroviruses which can be inactivated using the methods of the present invention include, for example, the HIV-1 and HIV-2 retroviruses as well as the other zinc finger containing retroviruses set forth in FIG. 1.

In yet another embodiment, the present invention provides a method of selecting a compound capable of dissociating a zinc ion chelated with a CCHC zinc finger of a retroviral nucleocapsid protein, the method comprising: contacting the CCHC zinc finger of the retroviral nucleocapsid protein with an electron acceptor; and (b) detecting the dissociation of the zinc ion from the CCHC zinc finger of the retroviral nucleocapsid protein. Such electron acceptors include:

disulfides having the formula R—S—S—R;
maleimides having the formula

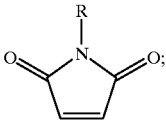

α-halogenated ketones having the formula

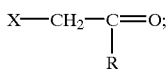

hydrazides having the formula R—NH—NH—R nitric oxide and derivatives containing the NO group;
cupric ions and complexes containing $Cu^{+2}$; and
ferric ions and complexes containing $Fe^{+3}$;
wherein R is any atom or molecule, and X is a halogen, e.g., F, I, Br and Cl. This selection method can be aided by detecting the dissociation of a zinc ion from the CCHC zinc finger of a retroviral nucleocapsid protein using a variety of methods including, for example, capillary electrophoresis, immuno-blotting, Nuclear Magnetic Resonance (NMR), high pressure liquid chromatography (HPLC), detecting release of radioactive zinc-65, detecting fluorescence, and detecting gel mobility shift.

In still another embodiment, the present invention provides numerous kits for selecting a compound capable of dissociating a zinc ion from a CCHC zinc finger of a retroviral nucleocapsid protein. Such kits include, for example, a retroviral nucleocapsid protein and instructions for detecting the dissociation of a zinc ion from a nucleocapsid protein. In addition, the kits can include a zinc ion chelated with a CCHC zinc finger of a retroviral nucleocapsid protein. An example of a retroviral nucleocapsid protein which can be included in such kits is the HIV-1 nucleocapsid protein derived from the HIV-1 retrovirus. The kits can also include a nucleocapsid protein incorporated in an intact retrovirus (such as HIV-1) or, alternatively, a nucleocapsid protein which is not complexed with an intact virus particle. The kit optionally includes instructions for the selection of a compound which can be used to inactivate a retrovirus, such compounds include the following:

disulfides having the formula R—S—S—R;
maleimides having the formula

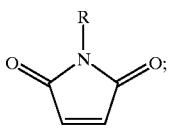

α-halogenated ketones with the structure

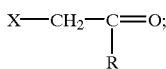

hydrazides having the formula R—NH—NH—R; nitric oxide and derivatives containing the NO group;
cupric ions and complexes containing $Cu^{+2}$; and
ferric ions and complexes containing $Fe^{+3}$;
wherein R is any atom or molecule, and X is selected from the group consisting of I, Br and Cl.

As mentioned, the kits will also include instructions for detecting the dissociation of a zinc ion from a retroviral nucleocapsid protein. Such instructions will be directed to detecting the dissociation of a zinc ion from the retroviral nucleocapsid protein using a method including, but not limited to, the following: capillary electrophoresis, immuno-blotting, Nuclear Magnetic Resonance (NMR), high pressure liquid chromatography (HPLC), detecting release of radioactive zinc-65, detecting fluorescence, and detecting a gel mobility shift.

Other features, objects and advantages of the invention and its preferred embodiments will become apparent from the detailed description which follows.

BRIEF DESCRIPTION OF THE DRAWINGS

FIG. 4 illustrates a model for the reaction of NEM with the CCHC zinc fingers of HIV-1.

FIG. 6 sets forth the results of reactions of HIV-1 NC retroviral CCHC zinc fingers with eight compounds.

FIG. 7 illustrates the functional groups known to react with retroviral zinc fingers.

FIG. 14 illustrates the chemistry of the thiurams.

DEFINITIONS

Figure 1:
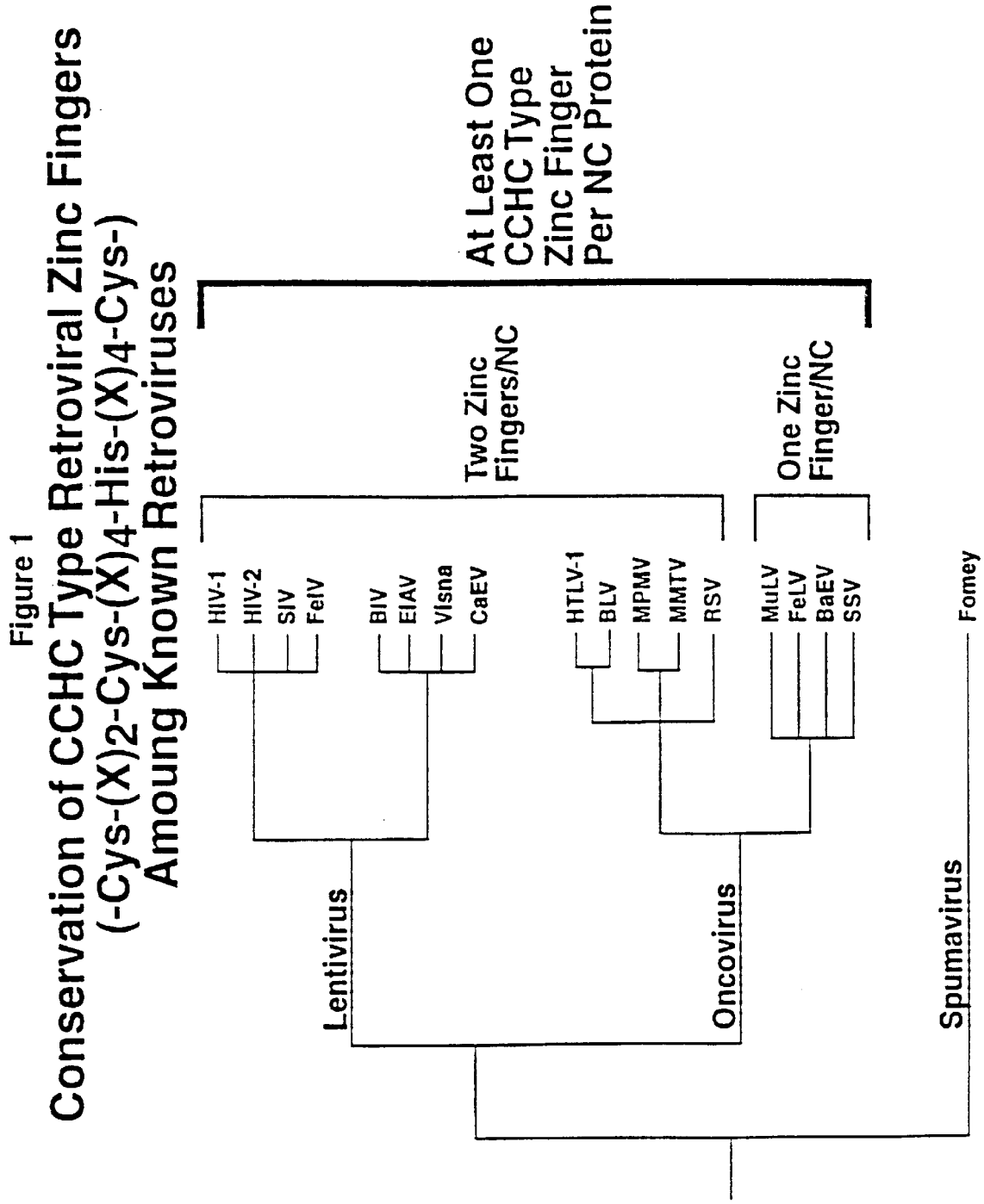
FIG. 1 illustrates the conservation of CCHC type retroviral zinc fingers among known retroviruses.
Figure 2:
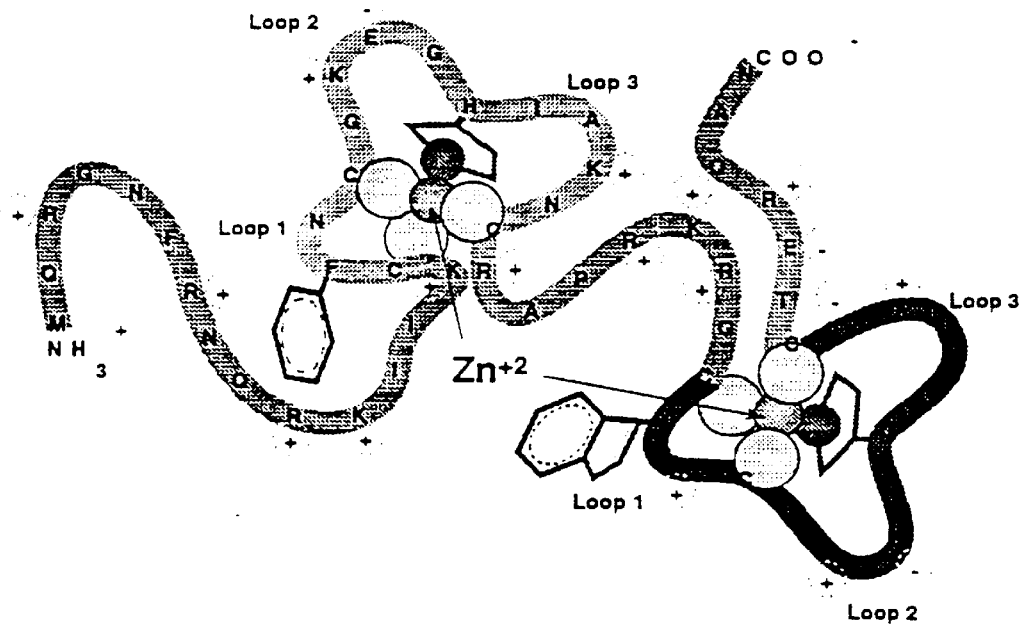
FIG. 2 illustrates a model of the CCHC zinc fingers of HIV-1$_{mn}$ nucleocapsid protein with zinc bound.

"Contacting" refers to the act of bringing components of a reaction into adequate proximity such that the reaction can occur. More particularly, as used herein, the term "contacting" can be used interchangeably with the following: combined with, added to, mixed with, passed over, flowed over, etc.

An "electron acceptor" is used herein to refer to an atom, ion or molecule capable of accepting one or more electron from the CCHC zinc finger region of a retroviral nucleocapsid protein.

An "electron donor" is used herein to refer to the CCHC zinc finger region of a retroviral nucleocapsid protein, which is capable of donating one or more electron to an electron acceptor atom or molecule.

A "retrovirus," unless otherwise indicated, refers to a retrovirus which contains one or more CCHC-type zinc finger per nucleocapsid protein, such as HIV-1.

A "test compound" is used herein to refer to any compound that is being tested for its ability to disrupt the CCHC zinc fingers of a retroviral nucleocapsid protein.

DETAILED DESCRIPTION OF THE INVENTION AND PREFERRED EMBODIMENTS

Retroviruses, such as HIV, become rapidly resistant to drugs used to treat the retroviral infection. Nucleotide analogues, such-as AZT, ddI, ddC and ddT, which are commonly used to treat HIV infection are ineffective, in part, because the HIV-virus develops complete resistance to the drugs in a relatively short period of time. This extreme adaptability of HIV arises due to the high error rate of the reverse transcriptase enzyme responsible for transcribing the gene upon infection.

HIV is an example of a hyper-mutable virus, having diverged into two major subtypes, (HIV-1 and HIV-2), each of which has many subtypes. Recently, the use of multiple drugs against a single protein (convergent combination therapy) has been suggested as a strategy to prevent emergence of HIV-1 drug-resistant mutants. The HIV-1 NC protein is an ideal drug target, because the two zinc fingers represent uniquely conserved, indispensable sites on the same protein which can be attacked by a single drug. Simultaneous mutations in each finger would be required for the development of drug resistance, and the close proximity of the targets greatly reduces the probability of recombinatorial events.

Combination therapy is also directed against different structural elements of the retrovirus, and against different regulatory mechanisms. This includes, for example, compounds which disrupt retroviral NC zinc fingers, used in combination with anti-retroviral agents, such as protease inhibitors, and nucleotide analogues such as 3'-Azido-3'doxythymidine (AZT) and dideoxy Inosine (ddI) which disrupt the action of the retroviral polymerase.

HIV-1 zinc fingers exhibit a previously unrecognized susceptibility to electron acceptors such as oxidizing and alkylating reagents useful for developing new classes of anti-retroviral drugs. Cysteine thiols in each of the two zinc fingers are rapidly attacked by reagents such as $Cu^{+2}$, $Fe^{+3}$, C-nitroso compounds, disulfides, maleimides, α-halogenated ketones, hydrazids and nitric oxide derivatives, with simultaneous loss of the native protein structure. The initial electron transfer occurs between zinc-bound thiolates and the reagent. Treatment of intact HIV-1 with an oxidizing agent, such as 3-nitrosobenzamide, induces disulfide linkage of the nucleocapsid protein and inactivates viral infectivity through oxidation of the zinc fingers.

The reactions described herein for retroviral zinc fingers differ from more conventional redox reactions of metalloproteins and prosthetic groups where the bound metal cycles between oxidation states. The loss of electrons from CCHC zinc finger arrays, whether through oxidation or alkylation is likely permanent, and the resulting covalent modification of the zinc fingers (e.g., formation of non-native disulfide bridges in the NC protein) is irreversible under physiological conditions. The reactions also differ from oxidation of free sulfydryls because the electrons are donated directly from the intact zinc finger.

CCHC zinc fingers are conserved in retroviruses for nucleotide binding and are possibly also required for donating electrons at some stage in the replication cycle. This invention demonstrates that alkylating and oxidizing reagents and coupled redox reactions can be targeted towards the electron-donating reactivity of HIV-1 NC protein zinc fingers, thereby inactivating the virus.

Accordingly, the present invention provides a descriptive mechanism for the disruption of CCHC zinc fingers by several classes of chemical compounds. Moreover, kits which can be used to identify compounds that can react with and disrupt retroviral zinc fingers in the viral NC proteins are also provided. Compounds which can inactivate a retrovirus by reacting with and disrupting retroviral zinc fingers in the viral NC proteins are also provided.

General Methods

The present invention provides several classes of compounds which can be used to inactivate retroviruses, such as HIV-1, by attacking the CCHC zinc fingers of the viral nucleocapsid protein and ejecting the zinc therefrom. Moreover, kits for identifying compounds that can react with HIV-1 CCHC zinc fingers are also provided. In particular, the kits of the present invention describe a set of specific tests and reagents that can be used to screen and identify compounds based on their ability to react with and disrupt retroviral zinc fingers in the viral NC proteins. It will be readily apparent to those of skill in the art that once inactivated, the retrovirus can be used, for example, as vaccines, as prophylactics, or as components in standard ELISA assays for the diagnosis of retroviral infections.

The following discussion of the general methods which can be used in conjunction with the present invention is intended for illustrative purposes only. Other alternative methods and embodiments will be apparent to those of skill in the art upon review of this disclosure.

A. Capillary Zone Electrophoresis (CZE)

Retroviral NC proteins complex with two zinc ions, each with a formal charge of $^+2$. Reagents that react with the protein and remove the zinc ions cause a change in the confirmation and charge of the protein. Thus, the electrophoretic mobility of the reacted protein will differ from the mobility of the unreacted protein. Changes in electrophoretic mobility of the protein can easily be detected by the standard technique of capillary zone electrophoresis (CZE). For a general description of CZE, see, e.g., *Capillary Electrophoresis, Theory and Practice* (Academic Press, Inc. Grossman and Colburn (eds.) (1992)), which is incorporated herein by reference.

Generally, electrophoretic mobility of the protein (at a pH determined by the buffer in the capillary electrophoresis tube) is used to move the retroviral protein from a fixed starting position towards one electrode. The migration rate is monitored by e.g., UV absorption, e.g., at 215 nm. Sample tubes containing an appropriate amount of a solution comprising the retroviral NC protein of choice, with and without the compound to be tested for CCHC zinc finger inactivation, are placed in an automatic sample injector. At programmed intervals, samples are drawn into the capillary tube and the UV absorption is monitored. Unmodified retroviral NC protein gives a sharp peak of migrating protein passing the detector. Modifications of the protein, caused by reaction with the test compound of choice, are revealed by a change in the electrophoretic mobility of the reacted protein.

Capillary zone electrophoresis has the advantage of simple automation, since many different samples can be loaded and analyzed in successive runs. Each run requires about 10 minutes and each sample tube can be analyzed multiple times. An example of a kit utilizing CZE for analysis of selected compounds to be tested for CCHC zinc finger reactivity would contain about 100 micrograms (μg) of purified retroviral NC protein complexed with zinc in, for example, 1.0 ml of water, and could be used for approximately 1,000 testings.

B. Release Of Radioactive Zinc From Zinc-65 Labeled p7NC

Purified p7NC can be reconstituted with radioactive zinc-65 with a determined specific activity. By monitoring the release of radioactive zinc-65 caused by the reaction of a test compound with a retroviral NC protein, it is possible to determine the reactivity of the test compound.

A test compound can be added to a solution containing the NC protein complexed with radioactive zinc-65. Following the reaction, protein (reacted and unreacted) can be precipitated, for example, by immunoprecipitation or immunoadsorption methods using known antibodies, or by the addition of a calibrated amount of nucleic acid such that the NC protein saturates the binding sites on the nucleic acid matrix. Under conditions of low ionic strength, the saturated protein-nucleic acid complex forms a precipitate that can be removed by centrifugation. Alternatively, labeled nucleocapsid protein is attached to a solid support, and test reagents are added directly to the attached protein. Any reactions releasing zinc from the protein can be detected by the release of radioactive zinc-65 into the soluble supernatant. In addition, the [zinc-65]-NC can remain unbound in solution in a 96-well format, test reagents added, the protein harvested, and then the resultant decrease in label on the paper quantitated. These general procedures can be automated depending on the equipment available.

A kit supplying retroviral nucleocapsid protein and appropriate precipitating agents can be used to detect the ability of test compounds to remove zinc from the protein.

C. Release Of Radioactive Zinc From Zinc-65 Labeled Whole Virus

It has previously been published that zinc is present in virus in quantities nearly stoichiometric with CCHC zinc finger arrays (Bess et al., *J. Virol.* 66, 840 (1992)). Nearly all of the zinc is coordinated in the CCHC arrays (Summers et al., *Protein Science* 1, 563 (1992)). Therefore, zinc released from a virus derives from zinc previously coordinated in CCHC arrays, rather than from unrelated proteins or other non-specific associations with the virion.

Purified virus can be produced from cells cultured in the presence of added zinc-65. Labeled virus can be isolated and purified by density gradient centrifugation in the presence of added EDTA to remove any unbound zinc. The purified virus can be any retrovirus of interest including, but not limited to, HIV-1, HIV-2 or SIV.

Compounds to be tested can be added to the purified radioactive virus under conditions appropriate for the test compound of choice. Following the reaction and removal and/or inactivation of the reagent, the virus is disrupted by the addition of a non-ionic detergent (e.g., Triton X-100), and the viral core containing the NC protein complexed to nucleic acid is removed by centrifugation.

Radioactive zinc-65 released into the supernatant indicates that the test compound penetrated the intact virus and disrupted the NC protein-zinc complex. Kits to determine whether test compounds can remove retroviral NC-chelated zinc would contain, for example, intact retrovirus particles with radioactive zinc-65 incorporated into their NC proteins, appropriate reaction buffers and a non-ionic detergent.

C. Fluorescence-Based Detection Of Zinc Dissociation From Retroviral Nucleocapsid Protein Changes in the intrinsic fluorescence of aromatic protein moieties are commonly used to monitor a reaction which involves a change in protein conformation. In the present invention, fluorescence can be used to monitor the loss of zinc from retroviral nucleocapsid proteins. The intrinsic fluorescence of Trp-37 in the second zinc finger of HIV-1 NC protein has been used to monitor nucleic acid binding and conformation of the zinc finger complex (see, Summers, et al., *Protein Science* 1:563 (1992)).

Artificial fluorescent probes can also be incorporated into a protein to provide for the detection of changes in conformation. Polyethino-adenine, for example, has been used as a fluorescent nucleotide to measure the extent of NC protein binding (see, Karpel, et al., *J. Biol. Chem* 262, 4961 (1987)).

Finally, a variety of known fluorescent zinc chelators capable of complexing liberated zinc are used to monitor zinc loss. By monitoring the release of zinc from the CCHC zinc finger arrays, the effect of a given reagent is determined.

D. Detection Of Disulfide Cross-Linked NC Protein By Gel-Mobility Shift Assays

Purified concentrated retrovirus and antisera against the purified NC protein of the virus can be used to test the ability of a specific compound to penetrate the virus and react with the NC protein by forming disulfide complexes in the core of the virus. The compound is mixed with the whole retrovirus under reaction conditions appropriate for the compound. The virus is then removed from the reagent by centrifugation and disrupted in, e.g, standard SDS-PAGE sample buffer with (reduced) and without (non-reduced) 2-mercaptoethanol. The viral proteins are then separated by standard SDS-PAGE and the sample examined for the presence or absence of the monomeric NC protein in the non-reduced sample. Depending upon the virus used in the experiment and the conditions of electrophoresis, the NC protein can be visualized by protein staining methods, or by immuno-blot (e.g., western) methods. Compounds which react with the NC protein by attacking the zinc finger complexes and forming disulfide cross-linked products (i.e., which generate multimers in the mobility shift assay) inactivate the virus. Thus, compounds of interest (i.e., those which cause cross-linking) reduced the amount of monomeric NC protein detected. For example, it has been determined that 3-nitrosobenzamide (NOBA), Tetramethylthiuram Disulfide, Tetraethylthiuram Disulfide, Tetraisopropylthiuram Disulfide, Tetrabutylthiuram Disulfide, Dicyclopentamethylenethiuram Disulfide, Aldrithiol-22, 2-Dithiobis(Pyridine N-Oxide), and 2,2 Dithiobis(benzothiazole) (all commercially available from the Aldrich Chemical Company (Milwaukee, Wis.) caused a cross-linking of the HIV-1 NC protein which resulted in a gel-mobility shift (see Table 2).

Concomitantly, the drug treated virions are tested for activity. The virions are suspended in media (rather than solubilized) and added to target cells. The cultures are then examined to determine whether the virions are still active. To determine whether the treated virus particles are active, the cells are monitored for the presence of intracellularly-synthesized proviral DNA using, for example, the polymerase chain reaction (PCR) (W. G. Rice et al., *PNAS* 90, 9721 (1993)). Alternatively, cytoprotection assays can be used (O. Weislow et al., *J. Natl. Cancer Inst.* 81, 577 (1993)). Likewise, viral inactivation assays can be performed to quantitively compare the ability of compounds to inactivate retroviruses.

A kit incorporating the gel-mobility shift concept can be used to identify and study compounds which are able to penetrate intact virus and to induce disulfide cross-links in the viral NC proteins. Such a kit would contain, for example, purified concentrated retrovirus and appropriate size standards to monitor the change in mobility through the gel due to disulfide cross-linking. The kit can optionally include other components, such as antisera to the appropriate nucleocapsid protein E. High Pressure Liquid Chromatography (HPLC) Purified NC Proteins For Structural Characterization of Reaction Products Highly purified retroviral NC proteins can be produced by expression from vectors generated through recombinant DNA technology. These proteins when reconstituted with zinc (see, Summers, et al., *Protein Science* 1:563–567 (1992) for methods), provide the source of the NC proteins containing the zinc fingers that are the targets for attack by the compounds of this invention. When the zinc fingers in NC proteins react with identified compounds, the reaction produces a covalent change in the NC protein, and the modified protein can be separated from the unreacted protein by, for example, reversed phase HPLC.

Figure 5:
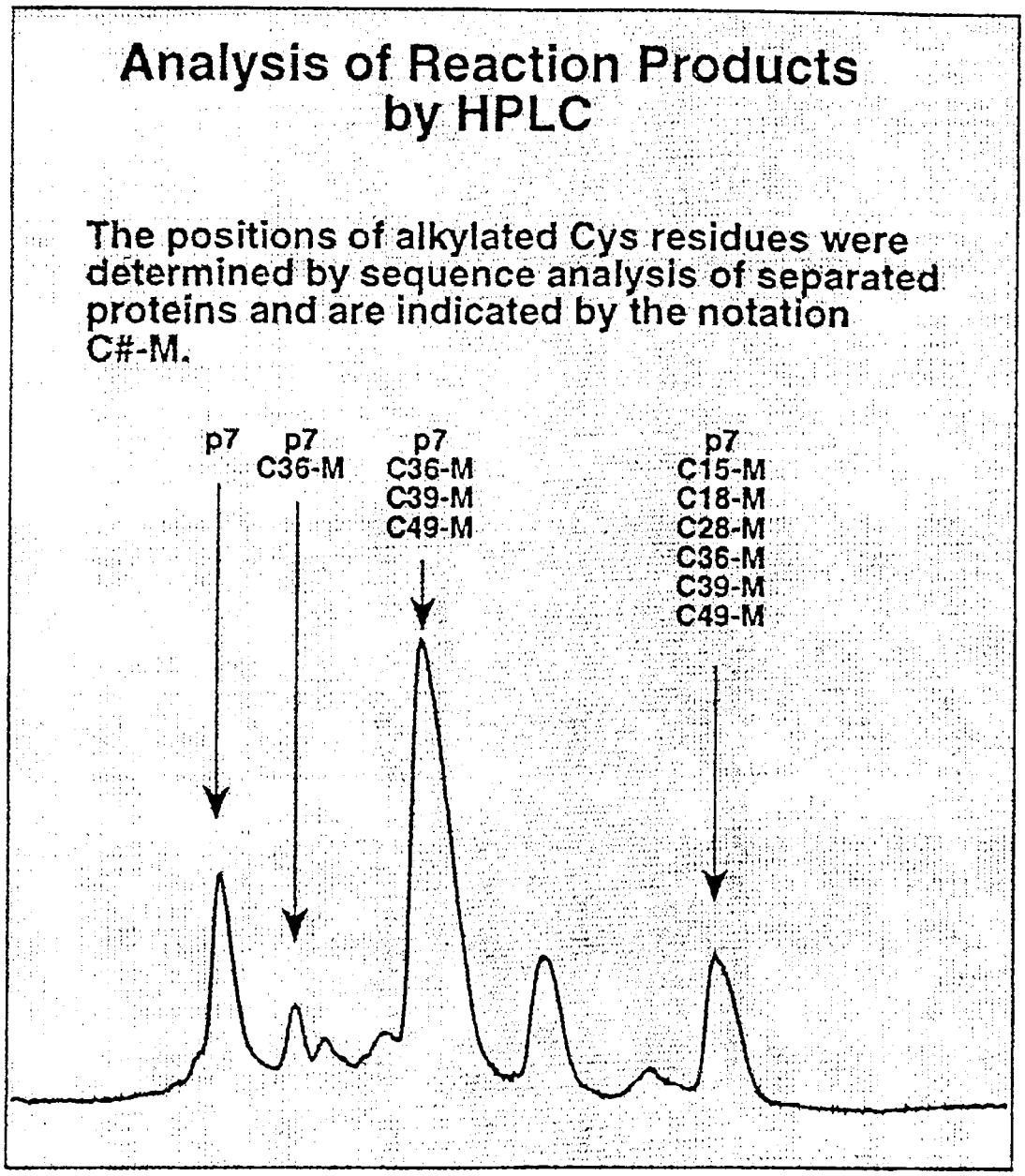
FIG. 5 illustrates an analysis of reaction products of p7NC with NEM by HPLC.

The purified proteins and these separation methods were used to obtain sufficient modified protein (i.e., products of the reaction) for chemical and structural analysis. An example of a HPLC separation of the protein products of the reaction of p7NC with various reagents N-ethyl maleimide is shown in FIG. 5, and the conditions for the reactions and the separations are given in the examples provided herein. The purified reaction products were isolated and their structures determined by standard N-terminal Edman degradation. However, for any specific reagent, the gradients and HPLC conditions will depend upon the NC protein and the reaction products.

This procedure has also been used to identify compounds which react with HIV-1 NC zinc fingers. The reaction conditions and HPLC conditions for the data presented were similar to those described above. The specific reagents tested are listed in FIG. 6 and Table 2, including non-reactive reagents tested using the same procedure. The data provided by these tests were used in constructing the list of reactive groups set forth in FIG. 7.

Kits standardizing these techniques are constructed such that they contain, for example, purified retroviral NC proteins.

F. Nuclear Magnetic Resonance (NMR)-Based Detection of Zinc Loss from Retroviral NC Proteins NMR can be used to monitor the loss of zinc from retroviral NC proteins (see, e.g., Rice, et al., *Nature* 361:473–475 (1993)). It is expected that one of skill is familiar with the general technique of NMR and its many applications to monitor protein-ligand interactions. Briefly, the atoms in retroviral NC proteins bound to zinc share a different local environment than NC proteins which lack zinc. The difference in local environment leads to distinct NMR spectra for protein molecules which bind zinc, versus those that do not. By monitoring, for example, the proton ($^1$H) spectrum of a sample containing zinc-chelated retroviral NC protein and a compound of the present invention over time, it is possible to measure whether the compound causes the protein to lose its zinc ion.

Since NMR can be used to provide the percent of protein molecules which are bound to zinc over time, it is also possible to use this technique to define the reaction kinetics of a given reaction. Similarly, NMR is used to monitor the effect of test compounds upon the binding of NC proteins to nucleic acid complexes. Kits containing e.g., purified retroviral NC proteins and oligonucleotides are used to standardize the practice of this method.

G. Structure Searching

This invention describes electron acceptors that are capable of oxidizing retroviral NC proteins. In order to find molecules having the structures described in the present invention, it is useful to compare the structures to the repertoire of known compounds. This can be performed by, for example, computer matching of chemical databases using commercially available databases and software or, alternatively, by inspection. Compounds can also be found by searching three-dimensional structures which allow docking with nucleocapsid proteins and nucleocapsid-nucleotide complexes.

Additionally, large chemical suppliers such as the Aldrich Chemical Company (Milwaukee, Wis.) and Sigma Co. (St Louis, Mo.) will perform chemical searches for specified reactive groups found in the compounds they sell. For example, a search of the Aldrich catalogue of chemical compounds revealed over 200 compounds with the functional groups described in this invention (not shown).

H. Cloning and Expression of Retroviral Nucleocapsid Proteins

Much of the nomenclature and general laboratory procedures required for the cloning and expression of retroviral nucleocapsid proteins in this application can be found in Sambrook, et al., Molecular Cloning *A Laboratory Manual* (2nd Ed.), Vol. 1–3, Cold Spring Harbor Laboratory, Cold Spring Harbor, N.Y., 1989. The manual is hereinafter referred to as "Sambrook, et al."

The nucleic acid compositions that are used to express retroviral nucleocapsid proteins, whether RNA, cDNA, genomic DNA, or a hybrid of the various combinations, can be isolated from natural sources, or synthesized in vitro. The nucleic acids are present in transformed or transfected whole cells, in a transformed or transfected cell lysate, or in a partially purified or substantially pure form.

Techniques for nucleic acid manipulation of genes encoding nucleocapsid proteins, such as subcloning nucleic acid sequences encoding NC protein fragments into expression vectors, labelling probes, DNA hybridization, and the like are described generally in Sambrook et al., supra, incorporated herein by reference.

Recombinant DNA techniques can be used to produce NC polypeptides. In general, the DNA encoding the NC fragment of interest are first cloned or isolated in a form suitable for ligation into an expression vector. After ligation, the vectors containing the DNA fragments or inserts are introduced into a suitable host cell for expression of the recombinant NC polypeptides. The polypeptides are then isolated from the host cells.

Once the NC DNAs are isolated and cloned, one can express the desired polypeptides in a recombinantly engineered cell such as bacteria, yeast, insect, or mammalian cells. It is expected that those of skill in the art are knowledgeable in the numerous expression systems available for expression of the recombinantly produced proteins. No attempt to describe in detail the various methods known for the expression of proteins in prokaryotes or eukaryotes will be made.

In brief summary, the expression of natural or synthetic nucleic acids encoding NC polypeptides will typically be achieved by operably lining the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the NC polypeptides. To obtain a high level expression of a cloned gene, it is desirable to construct expression plasmids which contain, at the minimum, a promoter to direct transcription, a ribosome binding site for translational initiation, and a transcription/translation terminator. The HIV-1 NC protein can be prepared as described in "Production of HIV-1 (MN) Nucleocapsid Protein (p7) by Recombinant DNA Technology" by Laura K. Busch (August 1994, as partial satisfaction of the requirements for the degree of MASTER OF SCIENCE in Biomedical Science From the Graduate School Department, Hood College Frederick, Md. Research Advisor: Louis E. Henderson, (hereinafter Busch)), which is incorporated herein by reference for all purposes.

I. Compound Chemistry

A study of the reaction mechanism of NC zinc displacement, presented for the first time in this application, reveals that CCHC zinc finger arrays act as selective electron donors and, thus, are capable of donating electrons to suitable electron acceptors. Compounds which accept electrons from the CCHC fingers, include:

disulfides having the formula R—S—S—R;

maleimides having the formula

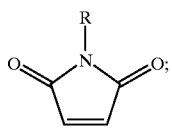

α-halogenated ketones having the formula

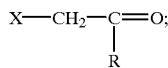

hydrazides having the formula R—NH—NH—R;

nitric oxide and derivatives containing the NO group;

nitroso compounds having the formula R—NO;

cupric ions and complexes containing $Cu^{+2}$; and

Ferric ions and complexes containing $Fe^{+3}$;

wherein R is any atom or molecule, and X is selected from the group consisting of I, Br and Cl.

No attempt is made herein to describe the synthesis of such compounds. Many of these compounds are commercially available and, if not, one of ordinary skill in the art will know how to synthesize them. Rather than providing synthetic mechanisms for the synthesis of the above electron acceptors, the present invention is directed to the use of such compounds to dissociate a zinc ion from a CCHC zinc finger of a retroviral nucleocapsid protein, which thereby inactivates the retrovirus. In addition, the present invention provides a method for screening compounds falling within the above classes of compounds to find those with the appropriate electron accepting structure.

J. Administration of compounds in vivo

The compounds of the present invention (i.e., those which inactivate retroviruses, as determined by the methods described herein) can be used to treat retrovirally-mediated diseases such as AIDS in patients. The compounds used in the present inventive method are administered in any suitable manner, preferably with pharmaceutically acceptable carriers. Suitable methods of administering such compounds in the context of the present invention to a patient are available, and, although more than one route can be used to administer a particular compound, a particular route can often provide a more immediate and more effective reaction than another route. It should be recognized that the administration of some of the compounds of the present invention are well-known for diseases other than those caused by retroviral infections (e.g., Tetraethylthiuram Disulfide is used in the treatment of alcoholism), and one of skill will be able to extrapolate the information available for use of these compounds to treat retroviral application such as AIDS.

Pharmaceutically acceptable carriers are determined in part by the particular compound being administered, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the compound dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the strength of the particular compound employed and the condition of the patient, as well as the body weight or surface area of the patient to be treated. The size of the dose also will be determined by the existence, nature, and extent of any adverse side-effects that accompany the administration of a particular compound in a particular patient. In determining the effective amount of the active ingredient to be administered in the treatment or prophylaxis of retrovirally-mediated diseases such as AIDS, the physician needs to evaluate circulating plasma levels, compound toxicities, and progression of the disease.

In the practice of this invention, the compounds can be administered, for example, by intravenous infusion, orally, topically, intraperitoneally, intravesically or intrathecally. The preferred method of administration will often be oral, rectal or intravenous, but the compounds can be applied in a suitable vehicle for the local and topical treatment of retrovirally-mediated conditions. Furthermore, since the compounds inactivate live retroviruses, they are suitable reagents to prevent transmission of retroviruses between an infected and an uninfected individual. For example, the compounds of the present invention can be used in vaginal cremes, or as components of spermicidal lubricants, e.g., in a vaginal suppository or a condom lubricant.

The compounds of this invention can supplement treatment of retrovirally-mediated conditions by any known conventional therapy, including cytotoxic agents, nucleotide analogues and biologic response modifiers.

For administration, compounds of the present invention can be administered at a rate determined by the LD-50 of the compound, and the side-effects of the compound at various concentrations, as applied to the mass and overall health of the patient. Administration can be accomplished via single or divided doses; however, in particularly preferred embodiments, the compounds will be administered in several divided doses.

K. Thiurams

The disulfide compound tetraethylthiuram disulfide (which is an approved drug for use in humans for the treatment of alcoholism) was tested for its ability to inhibit retroviral infectivity in vivo. Mice susceptible to the retrovirus SSFV (spleen focus forming virus) when injected with the virus die within 35–40 days as a result of virally-mediated transformation of cells of the spleen. Mice given oral doses of Tetraethylthiuram Disulfide survived SSFV infection significantly longer than mice which were infected with SSFV, but which were not treated with Tetraethylthiuram Disulfide.

Tetraethylthiuram disulfide was also found to inactivate HIV-1 virus using the PCR and viral inactivation assays described above. A number of tetraethylthiuram disulfide analogues, including formamidine disulfide dihydrochloride, O,O-diethyl dithiobis-(thioformate), isopropylxanthic disulfide, tetramethylthiuram disulfide, ethylthiuram disulfide, dicyclopentamethylenethiuram disulfide, tetraisopropyl-thiuram disulfide, and bis-(dibutyl: miocambamoyl) disulfide are also commercially available from, for example, The Aldrich Chemical Co.

Figure 13:
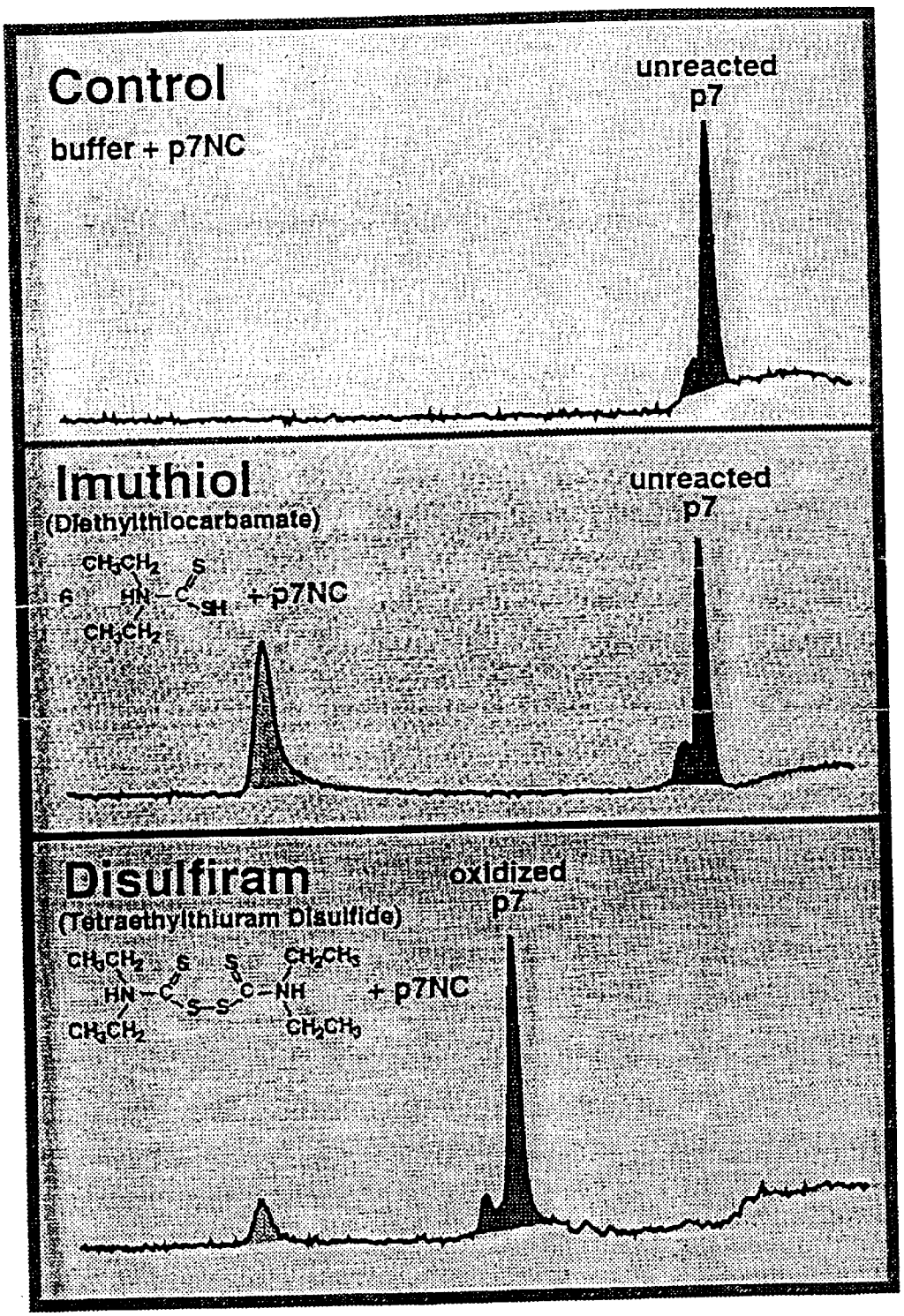
FIG. 13 illustrates the HPLC Analysis of p7NC with Imuthiol and Disulfiram.
Figure 15:
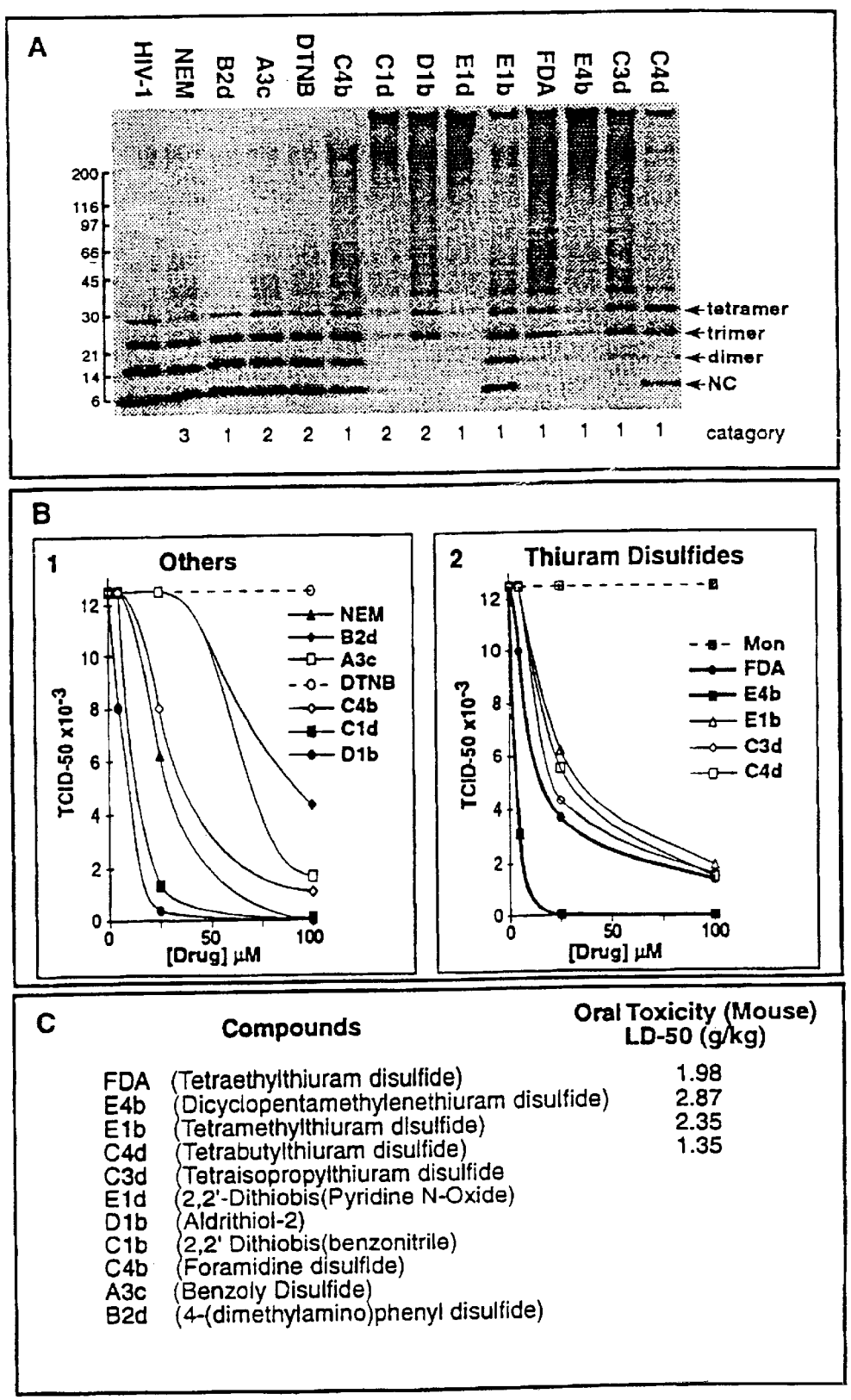
FIG. 15 is a composite figure with gel, virus inactivation, toxicity and names of compounds.

FIG. 14 summarizes some of the known chemistry of the thiurams using Tetraethylthiuram Disulfide and Diethylthiocarbamate as examples. Diethylthiocarbamate is sold under the trade name "Imuthiol" and is used as an immune stimulator. Tetraethylthiuram Disulfide is sold under trade names "Antabuse" and "Disulfiram" and is used to treat alcohol abuse. Tetraethylthiuram Disulfide is the disulfide form of Diethylthiocarbamate. Diethylthiocarbamate is also used to treat heavy metal toxicity. It can chelate divalent metal ions, including Zinc (see lower reaction). FIG. 13 (HPLC Analysis of p7NC with Imuthiol and Disulfiram) shows that the disulfide (Tetraethylthiuram Disulfide) reacts with p7NC to form oxidized p7 (disulfides) but Diethylthiocarbamate does not react with the protein. This shows that the reactive form is the disulfide. FIG. 15 (Composite with gel, virus inactivation, and toxicity and names of compounds) shows data demonstrating that thiurams and other compounds (see Panel C) can inactivate live virus (panel B) and cause cross linking of the NC protein (panel A). Tetraethylthiuram Disulfide inactivates the virus and cross links the NC protein, but Diethylthiocarbamate (panel B) does not. This shows that the virus inactivation is caused by the disulfide form of the compound and correlates with NC cross-linking.

Figure 12:
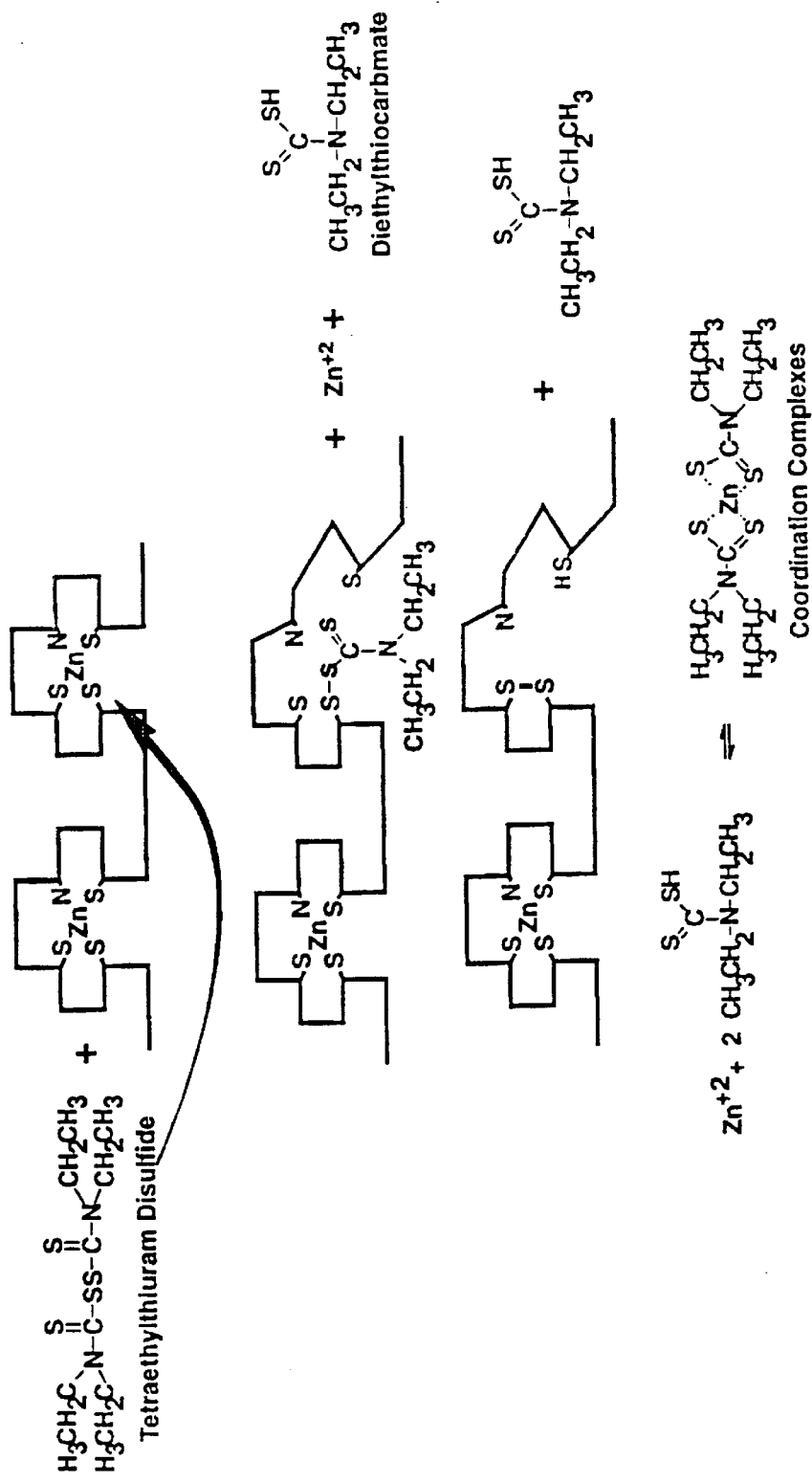
FIG. 12 illustrates reactions that occur in the viral core when the virus is inactivated by Tetraethylthiuram Disulfide.

FIG. 12 (reaction with zinc fingers) shows the reactions that occur in the viral core when the virus is inactivated by Tetraethylthiuram Disulfide. The reagent attacks the zinc fingers and the reaction proceeds through unstable mixed disulfides until the NC protein is oxidized and the reagent is reduced to Diethylthiocarbamate. The reaction liberates zinc from the protein and the Diethylthiocarbamate that is generated complexes with the released zinc. Thus, the thiuram disulfides have the added advantages of complexing the zinc once it is liberated.

EXAMPLES

The invention will be described in greater detail by way of specific examples. The following examples are offered for illustrative purposes, and are intended neither to limit or define the invention in any manner.

Example 1

Reaction of Recombinant p7NC with Cupric Chloride

The NC protein of HIV-1(MN) p7NC was expressed in *E. coli*. The coding sequence for HIV-1(MN) p7NC was cloned and expressed using an inducible *E. coli* promoter in the vector pMAL-c (New England Biolabs Inc., Beverly, Mass.). The protein was expressed as a maltose-binding fusion protein and released by proteolysis with Factor Xa. HIV-1(MN) p7NC was purified by HPLC and characterized, including complete amino acid sequence analysis. p7NC was purified by high-pressure liquid chromatography (HPLC) and reconstituted with two equivalents of zinc to generate native protein as described (M. F. Summers et al., *Protein Sci.* 1, 563 (1992)).

Coordination of $Zn^{+2}$ enhances the intrinsic fluorescence of the single tryptophan (Trp-37) in the second zinc finger. Incubation of p7NC with cupric chloride, ferric acetate or the C-nitroso compound 3-nitrosobenzamide (NOBA) resulted in a rapid biphasic decrease in fluorescence, suggesting disruption of the zinc fingers. The initial phase of the reaction with $Cu^{+2}$ ($T_{1/2}$<20 seconds) gave 70% quenching of the original fluorescence, followed by a much slower phase ($T_{1/2}$ ca. 6 minutes), resulting in a final limiting quenching of 85%.

The first quenching phase was a second order reaction, whereas the second phase was independent of protein concentration or oxidizing species. When $Zn^{+2}$ (in the protein) was replaced with $Cd^{+2}$, the reaction with $Cu^{+2}$ was still biphasic, but the first phase was much slower ($T_{1/2}$>5 minutes), indicating that the first phase was dependent on the coordinated metal ion.

Samples of p7NC and apo-p7 were reacted with varying amounts of cupric chloride and resulting products separated by HPLC. The reactions were carried out using 44.3 μM protein (p7NC or apo-p7) in 0.1 M Tris-HCl, pH 7.4, for 6 minutes at room temperature with varying concentrations of $CuCl_2$ to achieve the indicated ratios of reactants, in a final volume of 0.7 ml. Chromatography was carried out on the resulting products at pH 2 (0.05% trifluoroacetic acid) on μBondapak™ C-18 (3.9×300 mm) at 1.0 ml/minute using an acetonitrile gradient (0–17%, 20 ml; 17–20%, 60 ml;

20–60%, 10 ml). Elution positions of unreacted protein (p7NC or apo-p7) are indicated as apo-p7.

Figure 8:
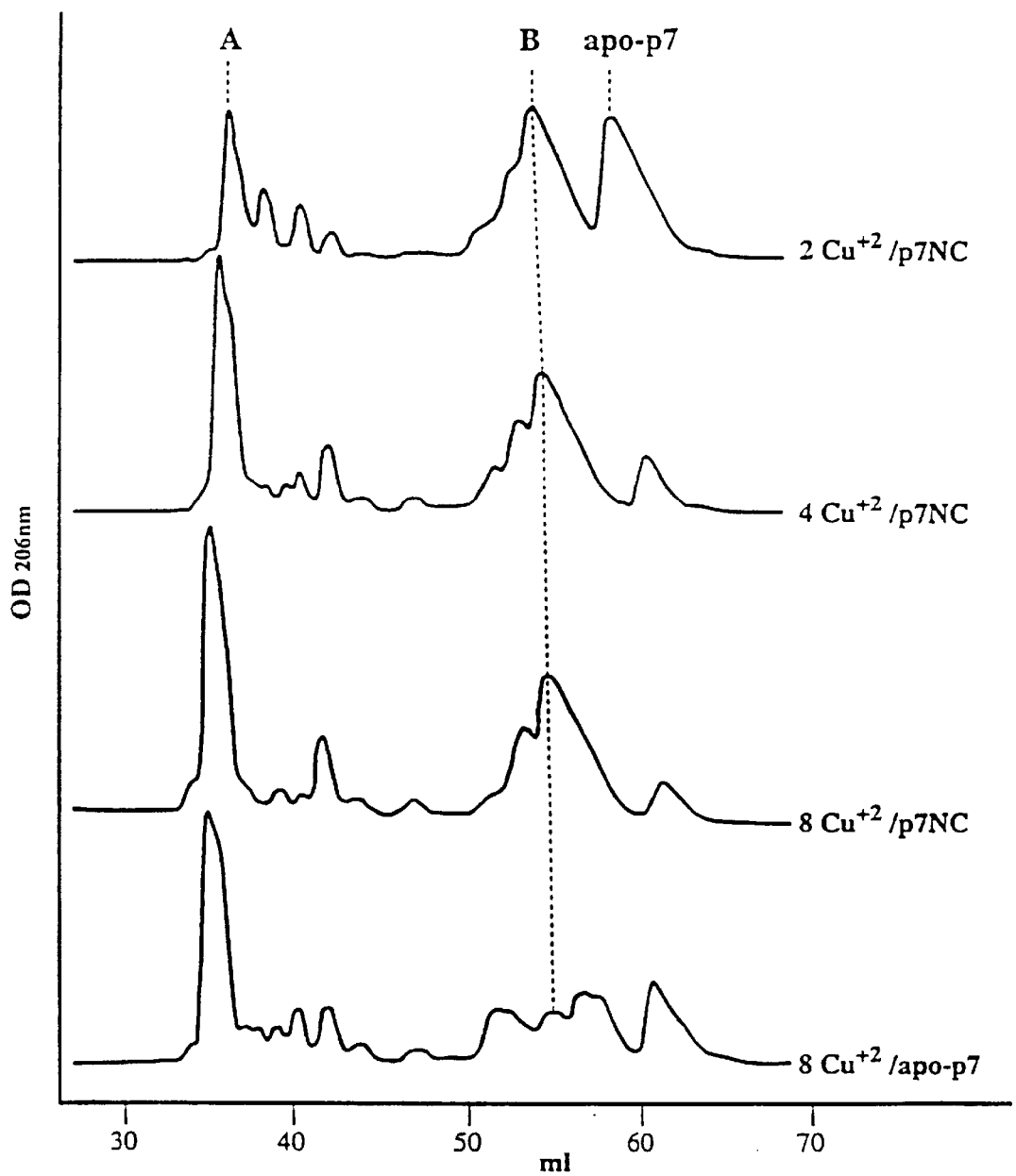
FIG. 8 illustrates the optical density profile of reverse phase HPLC separation of reacted p7NC and unreacted p7NC wherein the reaction with p7NC was performed with the indicated compound.

The disulfide bonded proteins elute in peaks A and B. Under chromatographic conditions (pH 2), zinc is lost from p7NC, and the protein elutes as apo-p7. With 2, 4 or 8 $Cu^{+2}$ per p7NC, approximately one half of the total protein was recovered in peak B (FIG. 8). Doubling the reaction time with an eight-fold excess of $Cu^{+2}$ did not change the amount of protein recovered in peak B. Conversely, protein recovered in peak A increased with increasing concentrations of $Cu^{+2}$ and increasing reaction time. Incubation of apo-p7 with $Cu^{+2}$ produced protein eluting as peak A and other products; however, only small amounts of protein were present in peak B. Thus, the amount of protein in peak B was dependent on the coordination of $Zn^{+2}$ in the p7NC. All peptide products appear to be disulfide-bonded forms of p7, since, following reduction with 2-mercaptoethanol, they eluted as apo-p7 (not shown).

Analyses by electrospray mass spectrometry (ES-MS) showed proteins that were 6 mass units (peak A) and 4 mass units (peak B) less than apo-p7, suggesting the presence of three (i.e., $p7(S—S)_3$) and two (i.e., $p7(S—S)_2(SH)_2$) intramolecular disulfide bonds, respectively. Since each disulfide requires that two thiolates donate an electron each to the acceptor ($Cu^{+2}+e- ->Cu^{+1}$), the results are consistent with reactions shown in equations 1 through 4.

$$p7NC^{-2}+2\ Cu^{+2}+4\ Cl^- -> [p7NC \cdot 2Cu^{+2}]^{+2} \cdot 2\ Cl^- +2\ Cl^- \quad 1)$$

$$4\ Cl^- +2\ [p7NC \cdot 2Cu^{+2}]^{+2} \cdot 2\ Cl^- ->^p 7(S—S)_2(SH)_2 + apo\text{-}p7 + 4\ Cu^{+1} + 4\ Zn^{+2} + 8\ Cl^- + 8\ OH^- \quad 2)$$

$$apo\text{-}p7 + 6\ Cu^{+2} -> p7(S—S)_3 + 6\ Cu^{+1} + 6\ H^+ \quad 3)$$

Initially, each of the two zinc fingers forms a complex with a $Cu^{+2}$ (Equation 1) and, subsequently, two complexes dismutate to $p7(S—S)_2(SH)_2$ and apo-p7 (Equation 2); this requires 4 $Cu^{+2}$ per molecule of $p7(S—S)_2(SH)_2$ formed and is consistent with the observation that half the total protein is recovered as $p7(S—S)_2$, regardless of the starting ratio of reactants. In the presence of additional $Cu^{+2}$, apo-p7 reacts to give $p7(S—S)_3$ (Equation 3). The overall reaction can be described by equation 4:

$$10\ Cu^{+2}+2\ p7NC^{-2} -> P7(S—S)_2(SH)_2 + p7(S—S)_3 + 10\ Cu^{+1} + 4\ Zn^{+2} + 2\ OH^- \quad 4)$$

Equation 4 is consistent with the kinetics of the reaction monitored by fluorescence of Trp-37, and suggests that the initial reaction associated with loss of the zinc-finger structure occurs via Equation 2, while the slower reaction occurs as shown in Equation 3.

Example 2
C-nitroso redox reactions with CCHC Zinc Fingers

Figure 9:
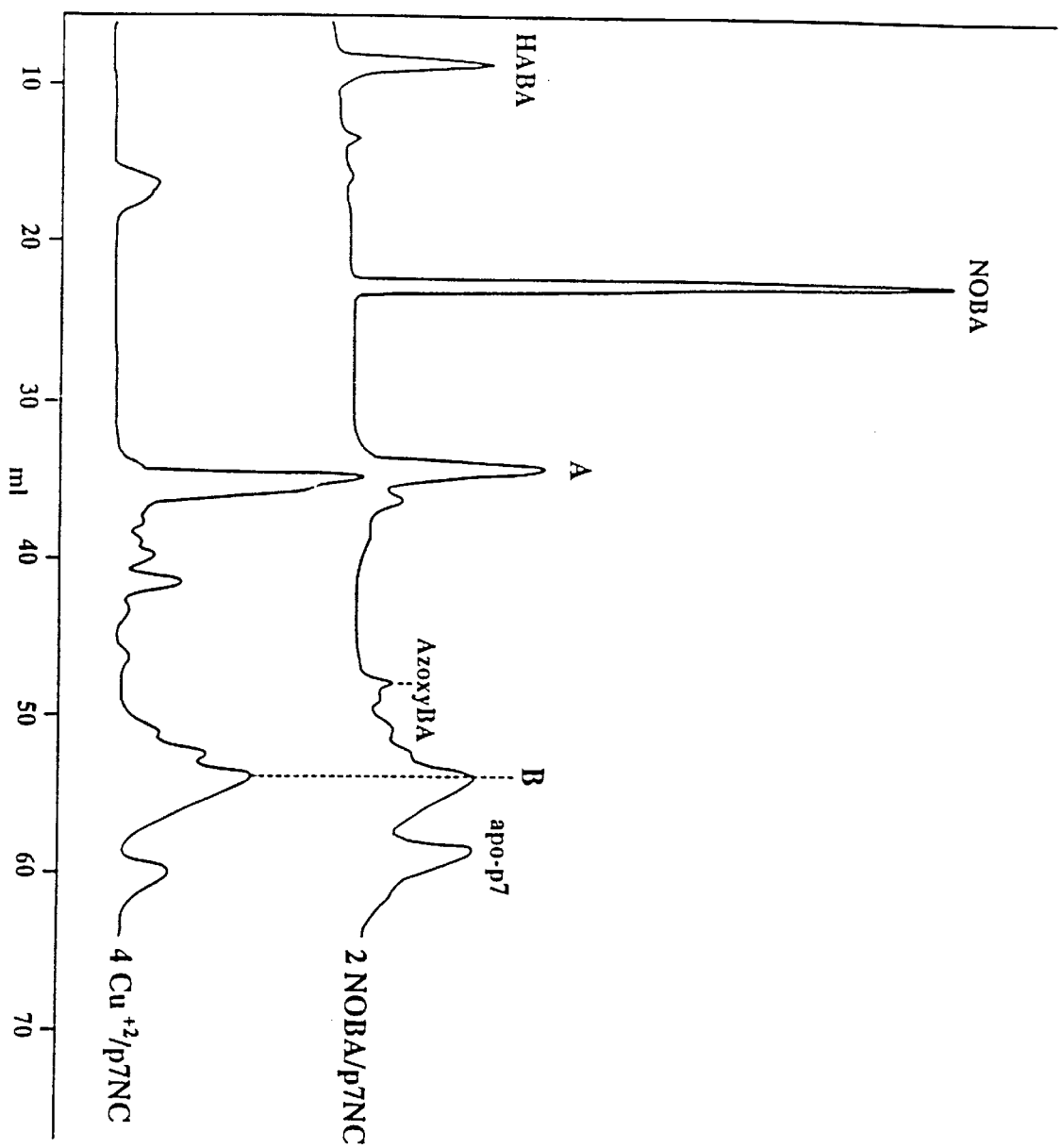
FIG. 9 illustrates the optical density profile of reverse phase HPLC separation of reacted p7NC and unreacted p7NC wherein the reaction with p7NC was performed with either NOBA or $Cu^{+2}$.

C-nitroso compounds (R—C—N=O) are known to accept two electrons in redox reactions with thiols (R'—SH) to form disulfides (R'—S—S—R') and hydroxylamines (R—C—NH—OH) via semimercaptal (SM) (R—C—(N—OH)—S—R') intermediates (M. K. Ellis, et al., *Chem. Biol. Interactions* 82:151 (1992)). Similarly, 3-nitrosobenzamide (NOBA) reacts with 2-mercaptoethanol to generate the corresponding products; however, hydroxylaminobenzamide (HABA) is unstable and can form NOBA, aminobenzamide, and azoxybenzamide (AzoxyBA). HABA was identified by its characteristic reaction products. HABA (FIG. 9) was collected, incubated at 37° C. (30 minutes) and analyzed by HPLC, showing dismutation products NOBA and aminobenzamide as well as AzoxyBA.

A two-fold excess of NOBA was reacted with p7NC, and the products were separated by HPLC (FIG. 10) as described above for $Cu^{+2}$ and p7NC. Elution positions for the reactants (NOBA and unreacted p7NC) and products, reacted p7NC, NOBA, HABA and AzoxyBA are indicated and an elution profile is included in FIG. 10. NOBA and AzoxyBA were supplied by Octamer, Inc. (Mill Valley, Calif.) and used as HPLC standards.

Figure 10:
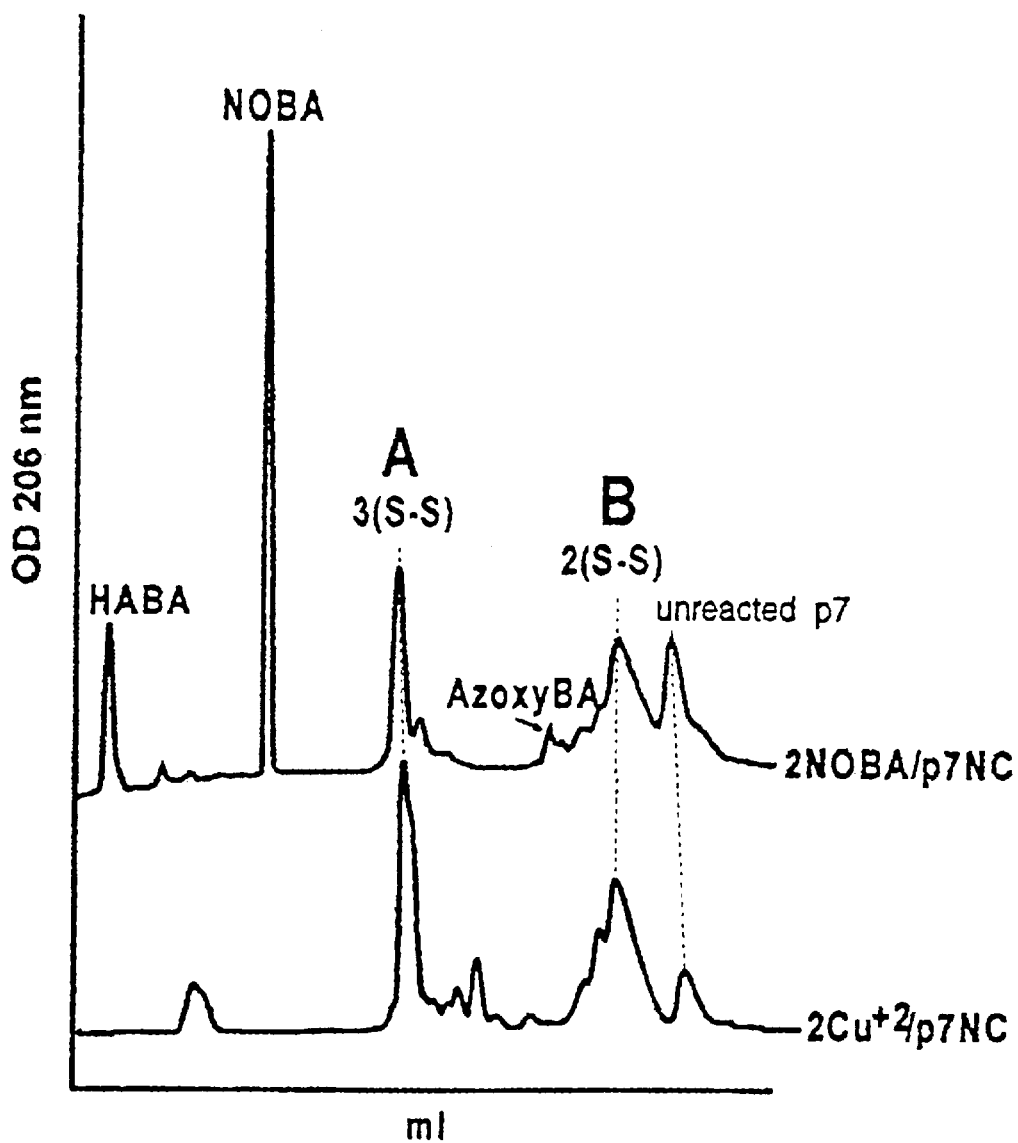
FIG. 10 illustrates the HPLC chromatograms of NOBA and cupric oxidation products of p7NC.
Figure 11:
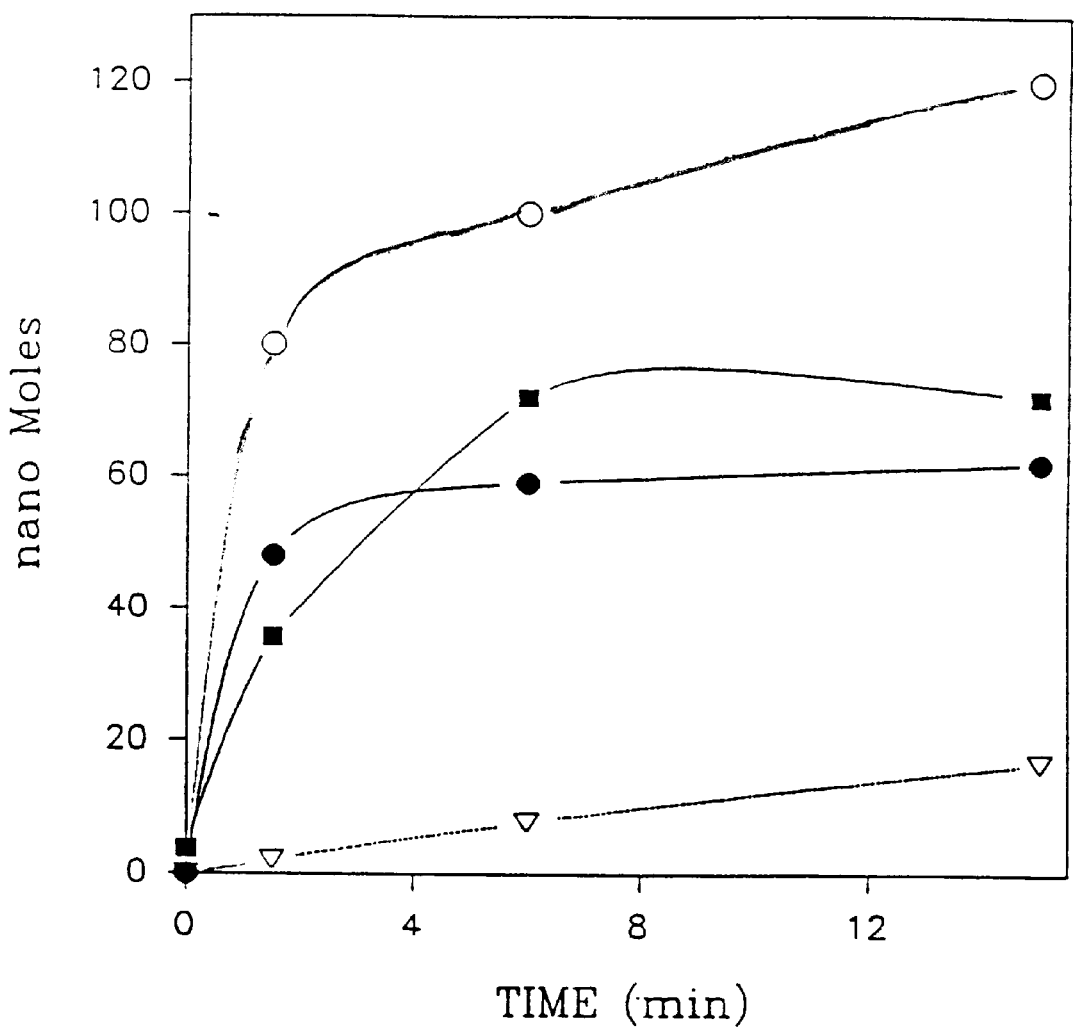
FIG. 11 illustrates a reaction profile quantitated over time by UV absorption at 206 nm by area and plotted as 2×p7NC (●) to reflect two zinc fingers per protein, NOBA ($E_{300}$ nm, 13214) (○), HABA ($E_{252}$ nm, 7600) (■) and AzoxyBA ($E_{318}$ nm, 13214) (▽).

NOBA oxidizes p7NC to products eluting as peaks A and B in FIG. 10. The elution positions for the other components (NOBA, HABA, and AzoxyBA) are also labeled. To study the time course for the reaction, p7NC was reacted with an eight-fold excess of NOBA for 1.5, 6, 15, and 45 minutes and analyzed by HPLC. Recovered products were also quantitated over time by UV absorption at 206 nm by area and plotted as 2×p7NC (●) to reflect two zinc fingers per protein, NOBA ($E_{300}$ nm, 13214) (○), HABA ($E_{252}$ nm, 7600) (■) and AzoxyBA ($E_{318}$ nm, 13214) (▽) (FIG. 11). An initial rapid reaction consuming at least 50 nanomoles of NOBA and 25 nanomoles of p7NC (50 nanomoles of zinc fingers), and generating at least 40 nanomoles of HABA, suggests that each of the two zinc fingers reacted rapidly to form HABA. The rapid phase was followed by a slower reaction involving the consumption of NOBA and HABA, and the production of AzoxyBA.

Protein eluting as peak B (FIG. 10) accumulated during the initial and intermediate stages of the reaction (up to 6 minutes), then slowly diminished as greater quantities of protein were recovered in peak A. As with $Cu^{+2}$, the amounts of protein recovered in peak B depended upon zinc coordination. To identify the protein products, HPLC fractions were analyzed by ES-MS. Peak A contained a single species with molecular mass of 6445.3±0.4 D (6 D less than native p7NC, 6451.5 D) (i.e., $p7(S—S)_3$). Peak B showed major components of 6448.0±1.9 D (i.e., $p7(S—S)_2(SH)_2$) and other components, 6600±2.6 D and 6749.3±3.2, suggesting species with one or two adducts of NOBA (150 D) adducts. The proteins eluting in peaks A and B were reduced with 2-mercaptoethanol, rechromatographed and identified as apo-p7.

Figure 3:
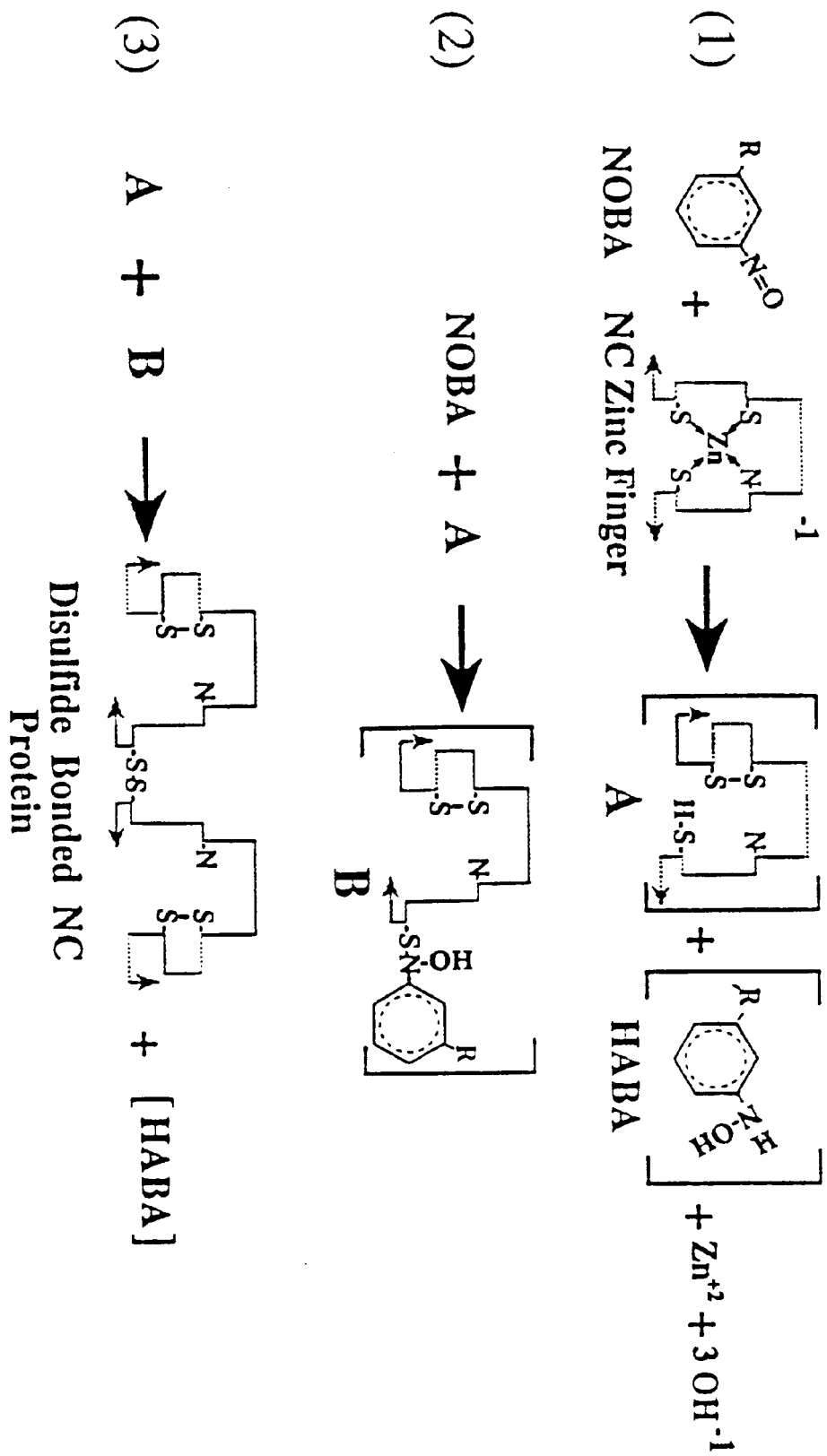
FIG. 3 illustrates a model for the reaction of NOBA with a CCHC zinc finger of a retrovirus.

A proposed reaction scheme accounting for the observed intermediates and products is shown in FIG. 3. In the first stage, thiolates in each of the two zinc fingers of p7NC donate electrons to form a disulfide (A in FIG. 3) with the elimination of zinc. This requires two electrons and can proceed via adducts in successive single-electron steps, or directly to HABA in a two-electron transfer. The data do not distinguish these possibilities; however, initial adducts (if formed) are short lived, because the rate of HABA production closely follows the rate of loss of p7NC zinc fingers. Remaining thiols are free to react with additional reagent to form adducts (B in FIG. 3 detected by ES-MS) that can proceed to react with free thiols to form other disulfides. The disulfide pattern depicted (FIG. 3) is arbitrary, but it is likely that specific disulfides are formed.

Example 3
Effect Of NOBA On HIV-1$_{MN}$

In order to determine whether HIV-1$_{MN}$ was inactivated by NOBA, the virus was incubated with varying concentrations of NOBA (3.0, 0.3, 0.03 and 0 mM) as in Table 1. The reaction products were pelleted by centrifugation, and separated by SDS-PAGE under reducing (2% 2-mercaptoethanol, panel A), or non-reducing conditions (panel B). p7NC was visualized by immunoblot analysis using monospecific rabbit antisera to the purified NC proteins as per L. E. Henderson et al., *J. Virol.* 66:1856 (1992).

The treatment of HIV-1$_{MN}$ with varying concentrations of NOBA demonstrated that the lowest concentration of reagent tested (0.03 mM; ratio of NOBA to zinc fingers was 50:1) inactivated greater than 99% of the virus (Table 1). Virus was removed from NOBA by centrifugation and analyzed by SDS-PAGE under reducing and non-reducing conditions. The proteins were detected by staining and immunoblot analysis with monospecific antisera to capsid (p24CA), matrix (p17MA), nucleccapsid (p7NC), transmembrane (gp41TM), and surface (gp120SU) proteins.

TABLE 1

Effect of NOBA on intact HIV-1. Cell free supernatants containing 6.2 μg p24/ml of HIV-1$_{MN}$ per ml were incubated for 2 hours with varying concentrations of NOBA. Viral particles were pelleted, resuspended in buffer and p24, zinc, and tissue culture infectious unit (TCIU/ml) determined.

| NOBA (mM) | p24(μg/ml) | TCIU/ml | Zn (μg/ml) |
|---|---|---|---|
| 0 | 91 | 3.2 × 10$^5$ | 0.23 |
| 0.03 | 90 | 1.0 × 10$^3$ | 0.21 |
| 0.3 | 83 | ND* | 0.21 |
| 3.0 | 58 | ND | 0.11 |

*None Detected

Under reducing conditions, the samples were indistinguishable (not shown). Under non-reducing conditions, the amounts of detected p7NC decreased with increasing NOBA concentration, while quantities of other proteins were unchanged (not shown). This is consistent with the reaction scheme outlined in FIG. 3, except that reaction conditions with viral-associated p7NC seem to favor intermolecular disulfides in the last step. This is due to the close associations among p7NC in the viral nucleocore.

In other experiments (not shown), zinc remained entrapped inside the viral lipid envelope and only escapes under conditions that also release p24CA. NOBA did not influence the bindings of virus to lymphocytes, the enzymatic activity of HIV-1 protease or levels of genomic RNA in the inactivated virus; however, the compound blocked proviral DNA synthesis without direct impairment of the reverse transcriptase enzyme (W. G. Rice et al., *PNAS* 90, 9721 (1993)). These data suggest that oxidation of p7NC inhibits infection by impairing reverse transcription and are consistent with the recent results from mutational analysis of HIV-1 zinc fingers by Gorelick et al., *J. Virol.* 64:3207 (1990).

Example 4
Reaction of Recombinant p7NC and intact HIV-1 virus with Disulfides

Disulfide reagents attack the zinc fingers of recombinant HIV NC protein (p7NC, prepared as described above) by acting as electron acceptors to NC cysteine residues and displacing the zinc ion. After the zinc ion is displaced, the thiolates derived from the disulfide reagent either remain bound to the sulfur atom on the NC cysteine residues (i.e., as adducts) or, alternatively, the thiolates leave the cysteines, which form new (and generally non-native) intra-protein disulfide links. In either case, the native structure of the NC protein is altered and the protein is rendered non-functional.

The disulfide reagent of choice (each available from the Aldrich Chemical Company (Milwaukee, Wis.)) was incubated for 10 minutes with purified p7NC protein (63 μM) at a ratio of 6 molecules of reagent to 1 molecule of NC protein (there are 6 cysteine thiols per NC protein). The formation of non-native protein conformations was monitored by HPLC as described above. The results (presented in Table 2, infra) show that a wide variety of disulfides inactivate the protein. Generally, the inactivation proceeds by formation of non-native, intra-protein disulfide links (designated "Disulfides"), but some of the reagents form adducts with the cysteine residues as well (designated "Adducts"). "Slow" reactions are those in which greater than 10% of the p7NC protein remained in its native form after the 10 minute incubation with reagent. "Very slow" reactions are those in which greater than 50% of the p7NC protein remained in its native form after the 10 minute incubation with reagent. "Fast" reactions result in complete transformation of the p7NC protein to non-native conformations during the 10 minute incubation period.

Disulfide reagents were further tested for their ability to disrupt NC structure in the virus, based on their ability to cause inter-NC cysteine disulfide bonds (i.e., cross-linking) in the intact virus. The formation of inter-NC cysteine disulfides creates NC multimers, which migrate through a non-reducing gel at a different rate than NC monomers, as described above. Intact HIV virus (generally 12.5 μM was exposed to the specified reagent (generally 25 μM for varying lengths of time and electrophoresed through a non-reducing SDS-polyacrylamide gel. HIV NC monomers and multimers were visualized by western blot analysis as described above in Example 3. The approximate time required to cross-link one-half of the NC proteins in the virus at the specified reaction conditions was then determined. The results, summarized in Table 2, infra show that a variety of disulfide reagents effectively cross-link the HIV NC protein in the intact virus. The top number in the cells of the X-link column in Table 2 refers to the approximate time in minutes required for one-half of the HIV NC proteins to become cross-linked.

Essentially the same strategy was employed to analyze the ability of the various disulfide reagents to cross-link the p1 Nucleocapsid Protein (p11NC) in intact Equine Infectious Anemia Virus (EIAV) particles. The advantages of working with EIAV include the fact that it is not a human pathogen, and that the p11NC protein can be visualized by simple coomassie-blue staining after performing the gel-mobility shift assay (rather than by western blotting as for HIV) described above. The reaction conditions were essentially the same for the EIAV assays as for the HIV assays described above, except that the concentration of virus and disulfide reagent was 4× the concentrations used in the HIV assay above. The second number in each cell in the X-link column in Table 2 represents the time required to cross-link one-half of the p11NC protein in the intact viral particles. The results show that a variety of disulfide reagents cross-link the p11NC protein in intact viral particles. The bottom number in each cell of the X-link column, unless otherwise indicated, represents the concentration of EIAV used in the assay. Blank cells throughout Table 2 indicate that the compound has yet to be tested for the specified property.

Several disulfide reagents were also tested for their ability to abolish HIV-1 infectivity in cell culture. Table 2 shows the concentration of reagent required to inactivate half of a standardized number of HIV-1 virus particles (about 10$^9$) in the tissue culture infectivity assay described above. The results show that disulfides inhibit HIV-1 in tissue culture (designated as "TCID (virus)" in Table 2, ). At least one of the disulfide reagents (Tetraethylthiuram Disulfide or "Antabuse," for treatment of alcoholism) is presently being used in Humans, and is generally well-tolerated.

Where known, the reagent's toxicity in mice (LD-50) is also shown in Table 2.

TABLE 2

Disulfide Reagents

| Compound | Toxicity (LD-50, TCID mouse) | Protein (Virus) | X-link (HPLC) | T-½ (min) |
|---|---|---|---|---|
| Tetramethylthiuram Disulfide | 1.35 g/kg (oral) 0.070 g/kg (IP) | | Disulfides (slow) | ~30 min ~15 min (50 μM) |
| Tetraethylthiuram Disulfide | 1.98 g/kg (oral) 0.075 g/kg (IP) | 66.0 μM | Disulfides | ~15 min ~15 min (50 μM) |
| Tetraisopropylthiuram Disulfide | | | Disulfides | >15 min ~15 min (50 μM) |
| Tetrabutylthiuram Disulfide | 2.35 g/kg (IP) | | Disulfides Adducts (slow) | ~30 min >60 min (50 μM) |
| Dicyclopentamethyl-enethiuram Disulfide | 2.87 g/kg (oral) | 4.0 μM | Disulfides | <<15 min ~10 min (50 μM) |
| Isopropylxanthic Disulfide | | | Disulfides | |
| O,O-Diethyl Dithiobis-Thioformate) | | | Disulfides Adducts | |
| Benzoyl Disulfide | | 68.0 μM | Disulfides Adducts | |
| Benzoylmethyl Disulfide | | | Adducts (very slow) | |
| Formamidine Disulfide. 2HCl | | 43.5 μM | Disulfides | |
| 2-(Diethylamino)ethyl Disulfide | | | Disulfides | |
| Aldrithiol-2 | | 9.0 μM | Disulfides Adducts (slow) | ~15 min ~15 min (50 μM) |
| Aldrithiol-4 | | | Disulfides | |
| 2,2-Dithiobis(Pyridine N-Oxide) | | | Disulfides | <<15 min <15 min (50 μM) |
| 6,6-Dithiodinicotinic Acid | | | Disulfides Adducts (slow) | ~60 min (HIV-1 @ 50 μM) |
| 4-Methyl-2-Quinolyl Disulfide | | | Disulfides Adducts (slow) | |
| 2-Quinolyl Disulfide | | | Disulfides Adducts (slow) | |
| 2,2 Dithiobis(ben-zothiazole) | 7.0 g/kg | | Disulfides | ~60 min HIV-1 @ 50 μM |
| 2,2-Dithiobis(4-Tert-Butyl-1-Isopropyl)-Imidazole | | | Disulfides | >>60 min HIV-1 @ 50 μM |
| 4-(dimethylamino)phenyl disulfide | | 17.5 μM | (negative) | |
| 2-Acetamidophenyl Disulfide | | | Disulfides (Adducts) | |
| 2,3-Dimethoxyphenyl Disulfide | | | Adducts (very slow) | |
| 4-Acetamidophenyl Disulfide | | | Disulfides (slow) | |
| 2-Ethoxycarboxamido)-phenyl Disulfide | | | Disulfides Adducts | |
| 3-Nitrophenyl Disulfide | | | Disulfides | |
| 4-Nitrophenyl Disulfide | | | Disulfides Adducts (slow) | |
| 2-Aminophenyl Disulfide | | | Disulfides Adducts (slow) | |
| 2,2 Dithiobis(ben-zonitrile) | | | Disulfides Adducts | <<15 min ~15 min (50 μM) |
| p-Tolyl Disulfoxide | | | Disulfides (slow) | |
| 2,4,5-Trichlorophenyl Disulfide | | | Disulfides (very slow) | |
| 4-Methylsulfonyl-2-Nitrophenyl Disulfide | | | Disulfides (slow) | |
| 4-Methylsulfonyl-2-Nitrophenyl Disulfide | | | Disulfides (very slow) | |
| 3,3-Dithiodipropionic Acid | | | Disulfides (slow) | |
| N,N-Diformyl-L-Cystine | | | Disulfides | |
| Trans-1,2-Dithiane-4,5-Diol | | | Disulfides (slow) | |
| 2-Chloro-5-Nitrophenyl Disulfide | | | Disulfides | |
| 2-Amino-4-Chlorophenyl Disulfide | | | Disulfides Adducts (fast) | |
| 5,5-Dithiobis(2-Nitrobenzoic Acid) | | | Disulfides Adducts (fast) | |
| 2,2-Dithiobis(1-Naphtylamine) | | | Disulfides Adducts (fast) | |
| 2,4-Dinitrophenyl p-Tolyl Disulfide | | | Disulfides Adducts (fast) | |
| 4-Nitrophenyl p-Tolyl Disulfide | | | Disulfides Adducts (slow) | |
| Thiamine Disulfide | (in use in humans) | anti-HIV activity in tissue culture | | |
| 4-Chloro-3-Nitrophenyl Disulfide | | | Disulfides Adducts | |

Example 5

N-ethylmaleimide NEM) Inactivates HIV

NEM (available from, e.g., the Aldrich Chemical Co.) was tested for its ability to alter the structure of p7NC as described above for disulfide reagents. No intra-chain disulfides were observed; rather, NEM was found to form adducts with the p7NC protein. As expected, no inter-protein NC cross-linking was observed when NEM was added to intact HIV. However, NEM blocks HIV infectivity in viral infectivity assays, presumably by adduct formation with the NC protein. The observed concentration that inactivated retroviral infectivity by 50% was 25 μM.

Example 6

2-(Carbamoylthio)-Acetic Acid 2-Phenylhydrazide Induces Disulfide Formation in p7NC Purified p7NC protein was treated with 2-(Carbamoylthio)-Acetic Acid 2-Phenylhydrazide as described above for the disulfide reagents of Example 4. Incubation of 2-(Carbamoylthio)-Acetic Acid 2-Phenylhydrazide with purified p7NC protein caused intra-chain disulfide formation, with most of the p7NC species present after a 10 minute incubation representing non-native conformations.

Example 7
Capillary Electrophoresis

The p7NC protein complexes two zinc ions, each with a formal charge of +2. Reagents that react with the protein and remove the zinc ions cause a change in the conformation and charge of the protein. Thus the electrophoretic mobility of the reacted protein will differ from the mobility of the unreacted protein. Changes in electrophoretic mobility of the protein can easily be detected by capillary zone electrophoresis (CZE).

The capillary column buffer was 0.001 M sodium phosphate at pH 3.0, and protein was detected by UV absorption at 215 nm. The sample tubes contained 10 or more microliters of a solution consisting of 0.25 micrograms of p7NC per ml in water at pH 7.0, with or without added 5'5'-dithiobis-(2-nitrobenzoic acid) DTNB. Sample tubes were placed in an automatic sample injector. At programmed intervals 10 µL of sample were drawn into the capillary column and the data was collected as UV absorption per minute. Unmodified p7NC gives a sharp peak of migrating protein passing the detector in about 7.95 minutes. Modifications of the protein, caused by reaction with the test compound of choice, are revealed by a change in this pattern.

Capillary electrophoresis has the advantage of simple automation, since many different samples can be loaded into the sample holding rack and analyzed in successive runs. Each run requires about 10 minutes and each sample tube can be analyzed many times.

A kit for practicing capillary electrophoresis would consist of eg., 100 micrograms of p7NC complexed with zinc in 1.0 ml of water and could be used for the testing of at least 1000 test compounds. This kit would be used to identify compounds capable of reacting with the purified NC protein.

The foregoing is offered for purposes of illustration. It will be readily apparent to those skilled in the art that the materials, procedural steps and other parameters of the methods and kits described herein can be further modified or substituted in ways without departing from the spirit and scope of the invention.

What is claimed is:

1. A method for dissociating a zinc ion from a CCHC zinc finger of a retroviral nucleocapsid protein, wherein the retroviral nucleocapsid protein comprises a structure $Cys(X)_2Cys(X)_4His(X)_4Cys$ which chelates a zinc ion, said method comprising the step of contacting said retroviral nucleocapsid protein with a compound selected from the group consisting of:

disulfides having the formula R—S—S—R;
maleimides having the formula

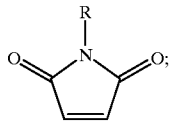

alpha-halogenated ketones having the formula

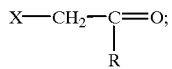

hydrazides having the formula R—NH—NH—R;
nitric oxide and derivatives containing the NO group;
cupric ions and complexes containing $Cu^{+2}$; and
ferric ions and complexes containing $Fe^{+3}$;
wherein the compound is not a C-nitroso compound of the formula R—C—NO, and wherein R is any atom or molecule, and X is selected from the group consisting of F, I, Br and Cl, wherein the compound contacts said retroviral nucleocapsid protein thereby causing dissociation of said zinc ion from said $Cys(X)_2Cys(X)_4His(X)_4Cys$ structure; and wherein contacting said retroviral nucleocapsid protein with said compound causes dissociation of said zinc ion from said retroviral nucleocapsid protein.

2. The method of claim 1, wherein said retroviral nucleocapsid protein is incorporated into an intact retrovirus.

3. The method of claim 1 wherein said retroviral nucleocapsid protein is an HIV-1 nucleocapsid protein.

4. The method of claim 1 further comprising detecting the dissociation of said zinc ion from the CCHC zinc finger of said retroviral nucleocapsid protein.

5. The method of claim 4 wherein detecting the dissociation of said zinc ion from the CCHC zinc finger of said retroviral nucleocapsid protein is carried out using a method selected from the group consisting of capillary electrophoresis, immuno-blotting, Nuclear Magnetic Resonance (NMR), high pressure liquid chromatography (HPLC), detecting release of radioactive zinc-65, detecting fluorescence, and detecting gel mobility shift.

6. A method for inactivating a retrovirus, wherein the retrovirus comprises a structure $Cys(X)_2Cys(X)_4His(X)_4Cys$ which chelates a zinc ion, said method comprising the step of contacting said retrovirus with a compound selected from the group consisting of:

disulfides having the formula R—S—S—R;
maleimides having the formula

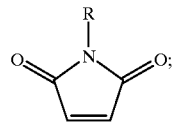

alpha-halogenated ketones having the formula

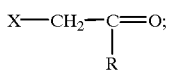

hydrazides having the formula R—NH—NH—R;
nitric oxide and derivatives containing the NO group;
cupric ions and complexes containing $Cu^{+2}$; and
ferric ions and complexes containing $Fe^{+3}$;
wherein the compound is not a C-nitroso compound of the formula R—C—NO, and wherein R is any atom or molecule, and X is selected from the group consisting of F, I, Br and Cl, wherein the compound contacts said retrovirus thereby causing dissociation of said zinc ion from said $Cys(X)_2Cys(X)_4His(X)_4Cys$ structure; and wherein contacting said retrovirus with said compound inactivates said retrovirus.

7. The method of claim 6, wherein said compound is selected from the group consisting of: Tetramethylthiuram Disulfide, Tetraethylthiuram Disulfide, Tetraisopropylthiuram Disulfide, Tetrabutylthiuram Disulfide, Dicyclopentamethylenethiuram Disulfide, Isopropylxanthic Disulfide, O,O-Diethyl Dithiobis-(Thioformate), Benzoyl Disulfide, Benzoylmethyl Disulfide, Formamidine Disulfide 2HCl, 2-(Diethylamino)ethyl Disulfide, Aldrithiol-2, Aldrithiol-4, 2,2-Dithiobis(Pyridine N-Oxide), 6,6-Dithiodinicotinic Acid, 4-Methyl-2-Quinolyl Disulfide, 2-Quinolyl Disulfide, 2,2 Dithiobis(benzothiazole), 2,2-Dithiobis(4-Tert-Butyl-1-Isopropyl)-Imidazole, 4-(dimethylamino)phenyl disulfide, 2-Acetamidophenyl Disulfide, 2,3-Dimethoxyphenyl Disulfide, 4-Acetamidophenyl Disulfide, 2-(Ethoxycarboxamido)phenyl Disulfide, 3-Nitrophenyl Disulfide, 4-Nitrophenyl Disulfide, 2-Aminophenyl Disulfide, 2,2 Dithiobis(benzonitrile), p-Tolyl Disulfoxide, 2,4,5-Trichlorophenyl Disulfide, 4-Methylsulfonyl-2-Nitrophenyl Disulfide, 4-Methylsulfonyl-2-Nitrophenyl Disulfide, 3,3-Dithiodipropionic Acid, N,N-Diformyl-L-Cystine, Trans-1,2-Dithiane-4,5-Diol, 2-Chloro-5-Nitrophenyl Disulfide, 2-Amino-4-Chlorophenyl Disulfide, 5,5-Dithiobis(2-Nitrobenzoic Acid), 2,2-Dithiobis(1-Naphtylamine), 2,4-Dinitrophenyl p-Tolyl Disulfide, 4-Nitrophenyl p-Tolyl Disulfide, and 4-Chloro-3-Nitrophenyl Disulfideformamidine disulfide dihydrochloride.

8. The method of claim 6, wherein said retrovirus is selected from the group consisting of Lentiviruses and Oncoviruses.

9. The method of claim 6, wherein said retrovirus is a HIV-1 retrovirus.

10. The method of claim 6, wherein the method further comprises contacting said retrovirus with an anti-retroviral agent.

11. The method of claim 6, wherein the method further comprises contacting said retrovirus with a nucleotide analogue.

12. The method of claim 6, wherein the method further comprises contacting said retrovirus with AZT.

13. A method of selecting a compound capable of dissociating a zinc ion chelated with a CCHC zinc finger of a retroviral nucleocapsid protein, said method comprising:

(a) contacting the CCHC zinc finger of said retroviral nucleocapsid protein with an electron acceptor; and (b) detecting the dissociation of said zinc ion from the CCHC zinc finger of said retroviral nucleocapsid protein, wherein said electron acceptor is a compound selected from the group consisting of disulfides having the formula R—S—S—R;
maleimides having the formula

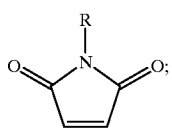

α-halogenated ketones having the formula

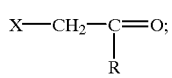

hydrazides having the formula R—NH—NH—R;
nitric oxide and derivatives containing the NO group;
cupric ions and complexes containing $Cu^{+2}$; and
ferric ions and complexes containing $Fe^{+3}$;
wherein the compound is not a C-nitroso compound of the formula R—C—NO, and wherein R is any atom or molecule, and X is selected from the group consisting of F, I, Br and Cl.

14. The method of claim 13, wherein said electron acceptor is a compound selected from the group consisting of Tetramethylthiuram Disulfide, Tetraethylthiuram Disulfide, Tetraisopropylthiuram Disulfide, Tetrabutulthiuram Disulfide, Dicyclopentamethylenethiuram Disulfide, Isopropylxanthic Disulfide, O,O-Diethyl Dithiobis-(Thioformate), Benzoyl Disulfide, Benzoylmethyl Disulfide, Formamidine Disulfide 2HCl, 2-(Diethylamino)ethyl Disulfide, Aldrithiol-2, Aldrithiol-4, 2,2-Dithiobis(Pyridine N-Oxide), 6,6-Dithiodinicotinic Acid, 4-Methyl-2-Quinolyl Disulfide, 2-Quinolyl Disulfide, 2,2 Dithiobis(benzothiazole), 2,2-Dithiobis(4-Tert-Butyl-1-Isopropyl)-Imidazole, 4-(dimethylamino)phenyl disulfide, 2-Acetamidophenyl Disulfide, 2,3-Dimethoxyphenyl Disulfide, 4Acetamidophenyl Disulfide, 2-(Ethoxycarboxamido)phenyl Disulfide, 3-Nitrophenyl Disulfide, 4-Nitrophenyl Disulfide, 2-Aminophenyl Disulfide, 2,2 Dithiobis(benzonitrile), p-Tolyl Disulfoxide, 2,4,5-Trichlorophenyl Disulfide, 4Methylsulfonyl-2-Nitrophenyl Disulfide, 4-Methylsulfonyl-2-Nitrophenyl Disulfide, 3,3-Dithiodipropionic Acid, N,N-Diformyl-L-Cystine, Trans-1, 2-Dithiane-4,5-Diol, 2-Chloro-5-Nitrophenyl Disulfide, 2-Amino4Chlorophenyl Disulfide, 5,5-Dithiobis(2-Nitrobenzoic Acid), 2,2-Dithiobis(1-Naphtylamine), 2,4-Dinitrophenyl p-Tolyl Disulfide, 4Nitrophenyl p-Tolyl Disulfide, and 4-Chloro-3-Nitrophenyl Disulfideformamidine disulfide dihydrochloride.

15. The method of claim 13 wherein said step of detecting the dissociation of said zinc ion from the CCHC zinc finger of said retroviral nucleocapsid protein is carried out using a method selected from the group consisting of capillary electrophoresis, immuno-blotting, Nuclear Magnetic Resonance (NMR), high pressure liquid chromatography (HPLC), detecting release of radioactive zinc-65, detecting fluorescence, and detecting gel mobility shift.

16. A kit for selecting a compound capable of dissociating a zinc ion from a CCHC zinc finger of a nucleocapsid protein, said kit comprising a retroviral nucleocapsid protein and instructions for detecting the dissociation of said zinc ion from said nucleocapsid protein, the instructions comprising directions for the selection of a compound selected from the group consisting of:

disulfides having the formula R—S—S—R;
maleimides having the formula

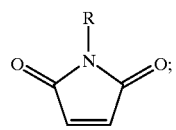

α-halogenated ketones with the structure

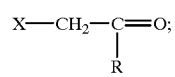

hydrazides having the formula R—NH—NH—R;
nitric oxide and derivatives containing the NO group;
cupric ions and complexes containing $Cu^{+2}$; and
ferric ions and complexes containing $Fe^{+3}$;
wherein the compound is not a C-nitroso compound of the formula R—C—NO, and wherein R is any atom or molecule, and X is selected from the group consisting of F, I, Br and Cl.

17. The kit of claim 16, wherein said retroviral nucleocapsid protein is supplied with the zinc ion chelated with the CCHC zinc finger of said retroviral nucleocapsid protein.

18. The kit of claim 16, wherein said retroviral nucleocapsid protein is derived from a HIV-1 retrovirus.

19. The kit of claim 16, wherein said nucleocapsid protein is incorporated in an intact retrovirus.

20. The kit of claim 19, wherein said retrovirus is selected from the group consisting of Lentiviruses and Oncoviruses.

21. The kit of claim 19, wherein said nucleocapsid protein is incorporated into an intact HIV-1 retrovirus.

22. The kit of claim 16, wherein said kit further comprises a disulfide compound selected from the group consisting of Tetramethylthiuram Disulfide, Tetraethylthiuram Disulfide, Tetraisopropylthiuram Disulfide, Tetrabutylthiuram Disulfide, Dicyclopentamethylenethiuram Disulfide, Isoropylxanthic Disulfide, O,O-Diethyl Dithiobis-(Thioformate), Benzoyl Disulfide, Benzoylmethyl Disulfide, Formamidine Disulfide 2HCl, 2-(Diethylamino)ethyl Disulfide, Aldrithiol-2, Aldrithiol-4, 2,2-Dithiobis(Pyridine N-Oxide), 6,6-Dithiodinicotinic Acid, 4-Methyl-2-Quinolyl Disulfide, 2-Ouinolyl Disulfide, 2,2 Dithiobis(benzothiazole), 2,2-Dithiobis(4-Tert-Butyl-1Isopropyl)-Imidazole, 4-(dimethylamino)phenyl disulfide, 2-Acetamidophenyl Disulfide, 2,3-Dimethoxyphenyl Disulfide, 4-Acetamidophenyl Disulfide, 2-(Ethoxycarboxamido)phenyl Disulfide, 3-Nitrophenyl Disulfide, 4-Nitrophenyl Disulfide, 2-Aminophenyl Disulfide, 2,2 Dithiobis(benzonitrile), p-Tolyl Disulfoxide, 2,4,5-Trichlorophenyl Disulfide, 4-Methylsulfonyl-2-Nitrophenyl Disulfide, 4-Methylsulfonyl-2-Nitrophenyl Disulfide, 3,3-Dithlodipropionic Acid, N,N-Diformyl-L-Cystine, Trans-1,2-Dithiane4,5-Diol, 2-Chloro-5-Nitrophenyl Disulfide, 2-Amino4Chlorophenyl Disulfide, 5,5-Dithiobis(2-Nitrobenzoic Acid), 2,2-Dithiobis(1-Naphtvlamine), 2,4-Dinitrophenyl p-Tolyl Disulfide, 4-Nitrophenyl p-Tolyl Disulfide, and 4-Chloro-3-Nitrophenyl Disulfideformamidine disulfide dihydrochloride.

23. The kit of claim 16, wherein said instructions are directed to detecting the dissociation of said zinc ion from said nucleocapsid protein using a method selected from the group consisting of capillary electrophoresis, immunoblotting, Nuclear Magnetic Resonance (NMR), high pressure liquid chromatography (HPLC), detecting release of radioactive zinc-65, detecting fluorescence and detecting a gel mobility shift.

24. The method of claim 1, wherein the compound is selected from the group consisting of: Tetramethylthiuram Disulfide, Tetraethylthiurarn Disulfide, Tetraisopropylthiuram Disulfide, Tetrabutylthiuram Disulfide, Dicyclopentamethylenethiuram Disulfide, Isopropylxanthic Disulfide, O,O-Diethyl Dithiobis-(Thioformate), Benzoyl Disulfide, Benzoylmethyl Disulfide, Formamidine Disulfide 2HCl, 2-(Diethylamino)ethyl Disulfide, Aldrithiol-2, Aldrithiol-4, 2,2-Dithiobis(Pyridine N-Oxide), 6,6-Dithiodinicotinic Acid, 4-Methyl-2-Quinolyl Disulfide, 2-Quinolyl Disulfide, 2,2 Dithiobis(benzothiazole), 2,2-Dithiobis(4-Tert-Butyl-1-Isopropyl)-Imidazole, 4-(dimethylamino)phenyl disulfide, 2-Acetamidophenyl Disulfide, 2,3-Dimethoxyphenyl Disulfide, 4-Acetamidophenyl Disulfide, 2-(Ethoxycarboxamido)phenyl Disulfide, 3-Nitrophenyl Disulfide, 4-Nitrophenyl Disulfide, 2-Aminophenyl Disulfide, 2,2 Dithiobis(benzonitrile), p-Tolyl Disulfoxide, 2,4,5-Trichlorophenyl Disulfide, 4-Methylsulfonyl-2-Nitrophenyl Disulfide, 4-Methylsulfonyl-2-Nitrophenyl Disulfide, 3,3-Dithiodipropionic Acid, N,N-Diformyl-L-Cystine, Trans-1,2-Dithiane4,5-Diol, 2-Chloro-5-Nitrophenyl Disulfide, 2-Amino-4-Chlorophenyl Disulfide, 5,5-Dithiobis(2-Nitrobenzoic Acid), 2,2-Dithiobis(1-Naphtylamine), 2,4-Dinitrophenyl p-Tolyl Disulfide, 4-Nitrophenyl p-Tolyl Disulfide, and 4-Chloro-3-Nitrophenyl Disulfideformamidine disulfide dihydrochloride.

25. The method of claim 1, wherein the compound selected from the group consisting of disulfides having the formula R—S—S—R.

26. The method of claim 1, wherein the compound is Aldrithiol-2.

27. The method of claim 6, wherein the compound selected from the group consisting of disulfides having the formula R—S—S—R.

28. The method of claim 6, wherein the compound is Aldrithiol-2.

* * * * *